United States Patent
Velis et al.

(10) Patent No.: US 11,173,004 B2
(45) Date of Patent: Nov. 16, 2021

(54) IN-VIVO ROBOTIC IMAGING, SENSING AND DEPLOYMENT DEVICES AND METHODS FOR MEDICAL SCAFFOLDS

(71) Applicant: Miraki Innovation Think Tank, LLC, Cambridge, MA (US)

(72) Inventors: Christopher J. Velis, Lexington, MA (US); Matthew P. Palmer, Medford, MA (US); Adeel Saleem Shafi, Cambridge, MA (US); Santosh Iyer, Somerville, MA (US)

(73) Assignee: MIRAKI INNOVATION THINK TANK, LLC, Cambridge, MA (US)

( * ) Notice: Subject to any disclaimer, the term of this patent is extended or adjusted under 35 U.S.C. 154(b) by 0 days.

(21) Appl. No.: 17/212,641

(22) Filed: Mar. 25, 2021

(65) Prior Publication Data
US 2021/0251704 A1 Aug. 19, 2021

Related U.S. Application Data

(63) Continuation of application No. PCT/US2019/052999, filed on Sep. 25, 2019.
(Continued)

(51) Int. Cl.
*A61B 34/30* (2016.01)
*B29C 64/209* (2017.01)
(Continued)

(52) U.S. Cl.
CPC ........ *A61B 34/30* (2016.02); *A61B 17/00234* (2013.01); *A61B 90/37* (2016.02);
(Continued)

(58) Field of Classification Search
CPC ... A61B 34/30; A61B 17/00234; A61B 90/37; A61B 2017/00296; A61B 2090/3762;
(Continued)

(56) References Cited

U.S. PATENT DOCUMENTS 5,741,248 A 4/1998 Stern et al.
5,807,395 A 9/1998 Mulier et al.
(Continued)

FOREIGN PATENT DOCUMENTS

CN 102688015 A 9/2012
CN 205322282 U 6/2016
(Continued)

OTHER PUBLICATIONS

Henry, A. and Bugos, G. Bubble, Crash & Recovery. 2010 [retrieved on Aug. 16, 2019]. Retrieved 7 from the Internet: <URL: https://books.google.com/books?id=ub6Zy2344KQC&pg=PA118&dq=block+medical+inc+homepump&hl=en&sa=X&ved=2ahUKEwjAgey976jkAhVBbKwKHaLoD8UQ6AEwAHoECAAQA0v=onepage&q=block%20medical°/020inc%20homepump&f=false> p. 119.
(Continued)

*Primary Examiner* — Hien N Nguyen
(74) *Attorney, Agent, or Firm* — Carter, DeLuca & Farrell LLP

(57) ABSTRACT

A multifunctional robotic system for performing in vivo procedures includes a control unit comprising a computer processor and a robotic arm in communication with the control unit for multi-axis movement of the robotic arm. The robotic arm has a plurality of passages therein. A printer head is disposed in one of the passages and is configured to create multi-dimensional objects in vivo. The robotic system includes a measuring system disposed in one of the passages. The computer processor has executable software configured to receive signals from the measuring system and is configured to control the printer head and the measuring system to position the object in an in vivo location based upon the signals from the measuring system.

29 Claims, 23 Drawing Sheets

Related U.S. Application Data

(60) Provisional application No. 62/736,232, filed on Sep. 25, 2018.

(51) Int. Cl.
  *A61B 90/00* (2016.01)
  *A61B 17/00* (2006.01)
  *B29C 64/379* (2017.01)

(52) U.S. Cl.
  CPC .......... *B29C 64/209* (2017.08); *B29C 64/379* (2017.08); *A61B 2017/00296* (2013.01); *A61B 2090/374* (2016.02); *A61B 2090/3762* (2016.02)

(58) Field of Classification Search
  CPC ............ A61B 2090/374; B29C 64/379; B29C 64/209
  See application file for complete search history.

(56) References Cited

U.S. PATENT DOCUMENTS

| | | | |
|---|---|---|---|
| 5,984,860 | A | 11/1999 | Shan |
| 6,240,312 | B1 | 5/2001 | Alfano et al. |
| 7,643,865 | B2 | 1/2010 | Iddan et al. |
| 7,658,736 | B2 | 2/2010 | von Alten |
| 8,021,384 | B2 | 9/2011 | Weiss et al. |
| 8,147,482 | B2 | 4/2012 | Shimizu et al. |
| 8,235,055 | B2 | 8/2012 | Mintchev et al. |
| 9,731,103 | B1 | 8/2017 | Rouse et al. |
| 2003/0060702 | A1 | 3/2003 | Kuth et al. |
| 2003/0167000 | A1 | 9/2003 | Mullick et al. |
| 2003/0181788 | A1 | 9/2003 | Yokoi et al. |
| 2003/0208107 | A1 | 11/2003 | Refael |
| 2003/0214580 | A1 | 11/2003 | Iddan |
| 2003/0216622 | A1 | 11/2003 | Meron et al. |
| 2004/0024392 | A1 | 2/2004 | Lewis et al. |
| 2005/0124898 | A1 | 6/2005 | Borovsky et al. |
| 2005/0148847 | A1 | 7/2005 | Uchiyama et al. |
| 2005/0256372 | A1 | 11/2005 | Yokoi et al. |
| 2006/0030754 | A1 | 2/2006 | Iddan |
| 2006/0265021 | A1 | 11/2006 | Herbert et al. |
| 2007/0032701 | A1 | 2/2007 | Fowler et al. |
| 2007/0123809 | A1 | 5/2007 | Weiss et al. |
| 2007/0142703 | A1 | 6/2007 | Lu |
| 2007/0156015 | A1 | 7/2007 | Gilad |
| 2007/0173691 | A1 | 7/2007 | Yokoi et al. |
| 2007/0299301 | A1 | 12/2007 | Uchiyama et al. |
| 2008/0194912 | A1 | 8/2008 | Trovato et al. |
| 2008/0199065 | A1 | 8/2008 | Swain |
| 2008/0269664 | A1 | 10/2008 | Trovato et al. |
| 2009/0125062 | A1 | 5/2009 | Amin |
| 2009/0182197 | A1 | 7/2009 | Goldwasser et al. |
| 2009/0234456 | A1 | 9/2009 | Nycz |
| 2010/0049012 | A1 | 2/2010 | Dijksman et al. |
| 2010/0113874 | A1 | 5/2010 | Quirini et al. |
| 2010/0145145 | A1 | 6/2010 | Shi et al. |
| 2011/0060189 | A1 | 3/2011 | Belson |
| 2011/0249105 | A1 | 10/2011 | Wilson et al. |
| 2013/0282173 | A1 | 10/2013 | Gunday et al. |
| 2013/0345670 | A1 | 12/2013 | Rajagopalan et al. |
| 2014/0081360 | A1 | 3/2014 | Ben-Yehuda et al. |
| 2014/0187862 | A1 | 7/2014 | Nishihara et al. |
| 2014/0243598 | A1 | 8/2014 | Genier et al. |
| 2015/0037445 | A1* | 2/2015 | Murphy ................ B29C 64/106 425/131.1 |
| 2015/0105797 | A1 | 4/2015 | Kim et al. |
| 2015/0105891 | A1* | 4/2015 | Golway ................ G06F 30/00 700/98 |
| 2015/0141750 | A1 | 5/2015 | Iddan et al. |
| 2015/0148599 | A1 | 5/2015 | Wilson et al. |
| 2015/0282797 | A1 | 10/2015 | O'Neil et al. |
| 2016/0166650 | A1 | 6/2016 | Imran |
| 2016/0288414 | A1* | 10/2016 | Ozbolat .............. A61F 2/30942 |
| 2016/0331209 | A1 | 11/2016 | Tearney et al. |
| 2017/0007154 | A1 | 1/2017 | Imran |
| 2017/0119235 | A1 | 5/2017 | Hyde et al. |
| 2017/0209029 | A1 | 7/2017 | Gazdzinski |
| 2017/0265807 | A1 | 9/2017 | Stopek |
| 2017/0291019 | A1 | 10/2017 | Dang et al. |
| 2017/0325932 | A1* | 11/2017 | Hoelzle ............... A61F 2/30756 |
| 2017/0335271 | A1* | 11/2017 | Maggiore .............. B33Y 10/00 |
| 2018/0000503 | A1 | 1/2018 | Baym et al. |
| 2018/0049725 | A1 | 2/2018 | Jones et al. |
| 2018/0098689 | A1 | 4/2018 | On |

FOREIGN PATENT DOCUMENTS

| | | |
|---|---|---|
| EP | 1408820 A2 | 4/2004 |
| EP | 2397101 A2 | 12/2011 |
| WO | 2006045011 A2 | 4/2006 |
| WO | 2008092376 A1 | 8/2008 |
| WO | 2015066705 A1 | 5/2015 |
| WO | 2016065205 A1 | 4/2016 |
| WO | 2017007821 A1 | 1/2017 |
| WO | 2017184839 A1 | 10/2017 |

OTHER PUBLICATIONS

International Search Report and Written Opinion of the International Searching Authority issued in corresponding Appl. No. PCT/US19/38697 dated Sep. 27, 2019 (9 pages).

Twin Pack Menthol Nasal Inhalers (scubsuk.com) 2015; figure 1; URL: <https://www.scrubsuk.com/twin-pack-menthol-nasal-inhalers.html>.

International Search Report issued in corresponding Appl. No. PCT/US19/24247 dated Jul. 17, 2019 (3 pages).

Written Opinion of the International Searching Authority issued in corresponding App. No. PCT/US19/24247 dated Jul. 17, 2019 (6 pages).

International Search Report dated Oct. 24, 2019 by the U.S. Patent and Trademark Office acting as International Searching Authority in International Application No. PCT/US2019/033697.

International Preliminary Report on Patentability dated Nov. 24, 2020 by the International Bureau on behalf of the U.S. Patent and Trademark Office acting as International Searching Authority in International Application No. PCT/US2019/033697.

International Preliminary Report on Patentability dated Nov. 24, 2020 by the International Bureau on behalf of the U.S. Patent and Trademark Office acting as International Searching Authority in International Application No. PCT/US19/33700.

International Search Report dated Aug. 14, 2019 by the U.S. Patent and Trademark Office acting as International Searching Authority in International Application No. PCT/US19/33700.

International Preliminary Report on Patentability dated Nov. 24, 2020 by the International Bureau on behalf of the U.S. Patent and Trademark Office acting as International Searching Authority in International Application No. PCT/US2019/033702.

International Search Report dated Aug. 16, 2019 by the U.S. Patent and Trademark Office acting as International Searching Authority in International Application No. PCT/US2019/033702.

International Preliminary Report on Patentability dated Dec. 8, 2020 by the International Bureau on behalf of the U.S. Patent and Trademark Office acting as International Searching Authority in International Application No. PCT/US2019/035318.

International Search Report dated Aug. 23, 2019 by the U.S. Patent and Trademark Office acting as International Searching Authority in International Application No. PCT/US2019/035318.

International Preliminary Report on Patentability dated Dec. 29, 2020 by the International Bureau on behalf of the U.S. Patent and Trademark Office acting as International Searching Authority in International Application No. PCT/US2019/038695.

International Search Report dated Nov. 5, 2019 by the U.S. Patent and Trademark Office acting as International Searching Authority in International Application No. PCT/US2019/038695.

International Preliminary Report on Patentability dated Dec. 29, 2020 by the International Bureau on behalf of the U.S. Patent and

(56) References Cited

OTHER PUBLICATIONS

Trademark Office acting as International Searching Authority in International Application No. PCT/US2019/038697.
International Search Report dated Apr. 2, 2020 by the U.S. Patent and Trademark Office acting as International Searching Authority in International Application No. PCT/US2019/052999.
International Search Report dated Dec. 18, 2020 by the U.S. Patent and Trademark Office acting as International Searching Authority in International Application No. PCT/US2020/052925.
International Preliminary Report on Patentability dated Sep. 29, 2020 by the International Bureau on behalf of the U.S. Patent and Trademark Office acting as International Searching Authority in International Application No. PCT/US2019/024247.
International Preliminary Report on Patentability dated Nov. 24, 2020 by the International Bureau on behalf of the U.S. Patent and Trademark Office acting as International Searching Authority in International Application No. PCT/US2019/033235.
International Search Report dated Aug. 2, 2019 by the U.S. Patent and Trademark Office acting as International Searching Authority in International Application No. PCT/US2019/033235.
International Preliminary Report on Patentability dated Nov. 24, 2020 by the International Bureau on behalf of the U.S. Patent and Trademark Office acting as International Searching Authority in International Application No. PCT/US2019/033236.
International Search Report dated Aug. 1, 2019 by the U.S. Patent and Trademark Office acting as International Searching Authority in International Application No. PCT/US2019/033236.
International Preliminary Report on Patentability dated Nov. 24, 2020 by the International Bureau on behalf of the U.S. Patent and Trademark Office acting as International Searching Authority in International Application No. PCT/US2019/033474.
International Search Report dated Aug. 9, 2019 by the U.S. Patent and Trademark Office acting as International Searching Authority in International Application No. PCT/US2019/033474.
International Preliminary Report on Patentability dated Nov. 24, 2020 by the International Bureau on behalf of the U.S. Patent and Trademark Office acting as International Searching Authority in International Application No. PCT/US2019/033475.
International Search Report dated Aug. 9, 2019 by the U.S. Patent and Trademark Office acting as International Searching Authority in International Application No. PCT/US2019/033475.
International Preliminary Report on Patentability dated Nov. 24, 2020 by the International Bureau on behalf of the U.S. Patent and Trademark Office acting as International Searching Authority in International Application No. PCT/US2019/033476.
International Search Report dated Sep. 5, 2019 by the U.S. Patent and Trademark Office acting as International Searching Authority in International Application No. PCT/US2019/033476.
International Preliminary Report on Patentability dated Nov. 24, 2020 by the International Bureau on behalf of the U.S. Patent and Trademark Office acting as International Searching Authority in International Application No. PCT/US2019/033696.
International Search Report dated Aug. 16, 2019 by the U.S. Patent and Trademark Office acting as International Searching Authority in International Application No. PCT/US2019/033696.
Written Opinion of the International Searching Authority issued in corresponding App. No. PCT/US19/052999 dated Apr. 2, 2020 (11 pages).
International Search Report dated Sep. 27, 2019 by the U.S. Patent and Trademark Office acting as International Searching Authority in International Application No. PCT/US2019/038697.
Korean language Office Action dated Aug. 12, 2021, by the Korean Intellectual Property Office in counterpart Korean patent application No. 10-2021-7011695, pp. 1-4.

* cited by examiner

IN-VIVO ROBOTIC IMAGING, SENSING AND DEPLOYMENT DEVICES AND METHODS FOR MEDICAL SCAFFOLDS

CROSS REFERENCE TO RELATED APPLICATION

This application is a Continuation of, and claims priority to and the benefit of, International Application No. PCT/US2019/052999, filed Sep. 25, 2019, which, in turn, claims the benefit of, and priority to, U.S. Provisional Application No. 62/736,232, filed Sep. 25, 2018. The entire contents of each of the foregoing applications are hereby incorporated by reference herein

FIELD OF THE INVENTION

The present invention relates generally to multi-function robotic systems for in vivo imaging, sensing and deployment of medical scaffolds, and more particularly to imaging and sensing implant sites within the human body to obtain patient specific implant site parameters, including dimensions, contours, physical characteristics and chemical properties and in vivo deploying medical scaffolds corresponding to the patient specific implant site parameters.

BACKGROUND OF THE INVENTION

Many orthopedic surgical procedures require the physician to implant a spacer between two adjacent bones to fill a void, correct a deformity, or maintain proper spacing. The goal is for these bones to ultimately fuse together. Traditionally, these spacers are inserted by first removing diseased or damaged tissue (e.g., the disc nucleus (soft bone marrow) or removing bone (e.g., spinal discs include the disc annulus (perimeter made of bone) to correct a deformity and then implanting the spacer between the adjacent bones. A plate and/or screws may be used to span the two bones and provide stability while the bone grows and fuses the two bones together.

Many different orthopedic procedures utilize spacers. Spacers are used in many orthopedic spine surgeries. Anterior cervical discectomy and fusion (ACDF) is a common cervical spine procedure where a herniated or degenerative disc is removed, and a spacer is inserted in its place. The goal of this procedure is for the two adjacent bones to fuse together, while the overall height of the spine is maintained (by the spacer). Similar procedures are performed in lumbar spine and may utilize either a posterior approach (Posterior Lumbar Interbody Fusion, PLIF) or a transforaminal approach (Transforaminal Lumbar Interbody Fusion, TLIF).

Additionally, spacers may be used for osteotomies of the medial cuneiform (Cotton Wedge) and for lengthening osteotomies of the metatarsals (Evans Wedge) and to correct varus or valgus deformities of the knee (High Tibial Osteotomy Wedges, HTO Wedge).

Spacers used in orthopedic procedures need to be made of biocompatible materials and be strong enough to support the loads applied to them. Often, they are manufactured from polymers, metal alloys, or biological tissue. Suitable polymers are typically in the polyaryl-ether-ketone (PAEK) family, with polyether-ether-ketone (PEEK) being the most commonly used polymer for spacers. Polymer materials have the advantage of being radiolucent so as not to be visible on x-ray while also having a Young's modulus more similar to bone so as to avoid stress shielding. Spacers are also commonly manufactured from titanium (CP-Ti) and titanium alloys (i.e., titanium 6-aluminum 4-vanadium (Ti-6-4)). Spacers may be manufactured from synthetic or allograft bone. Spacers may be made of solid (bulk) material or may be porous. Porous implants are advantageous as they allow for bone to grow into the implant and also reduce the Young's modulus of stiffer materials to be closer to that of bone.

While these implants do fulfill their biologic requirement of filling a gap between two bones, they are limited to fixed pre-manufactured sizes. While three-dimensional (3D) printing technology has advanced to allow for custom manufactured wedges, physicians remain limited by surgical site access, can only implant wedges that fit through and around the anatomy of the region, and need adequate lead time to allow for the wedge to be manufactured. Thus, improvements are desirable in this field of technology.

Problems with spinal implants include, but are not limited to when putting a cage in spinal disc space the clinician doesn't know if the cage is placed on center (soft marrow) or edges (hard cortical bone). Typical processes for implantation rely on x-ray alone to attempt to locate the implant. Spinal discs include a disc annulus (perimeter made of bone) and a disc nucleus (soft bone marrow). Often, the interface between bone and the implant is poor, which can result in weak or poor bone growth.

Conventional implants, medical scaffolds and spacers positioned between two bones, e.g., vertebral bones, often demonstrate movement and shifting once positioned between the bones. The movement and shifting can occur due to patient movement, incorrect placement, and/or use of standard size implants or spacers that do not comport with the dimensions and configuration of the cavity between the vertebra and contours of the surface of the vertebra. The vertebra are formed by a central trabecular bone (i.e., soft bone) surrounded by cortical bone (i.e., dense or hard bone). The trabecular bone is exposed on axial ends of the vertebra and the cortical bone extends circumferential therearound. The implants, medical scaffolds and spacers must be supported in the cavity by the cortical bone and be maintained spaced apart from the trabecular bone. However, the movement and shifting of the implants, medical scaffolds and spacers can cause the implants, medical scaffolds and spacers to displace into the trabecular bone. Such shifting results in improper spacing of the vertebra and causes the patient to suffer pain. Thus, improvements are desirable in this technology to maintain the positioning of the spacer or implant.

SUMMARY

There is disclosed herein a multifunctional robotic system for performing in vivo procedures. The robotic system includes a control unit that has a computer processor. The multifunctional robotic system includes a robotic arm that is in communication with the control unit for multi-axis movement of the robotic arm. The robotic arm includes a casing having a plurality of passages therein. A printer head is disposed in and is operable from one or more of the plurality of passages. The printer head is configured to create one or more multi-dimensional objects. The multifunctional system includes a measuring system that is disposed in and is operable from one or more of the plurality of passages. The computer processor is in communication with the printer head and the measuring system. The computer processor has executable software configured to receive signals from the measuring system. The executable software is configured to control the printer head and the measuring system to position the object in an in vivo location based upon the signals from the measuring system.

In one embodiment, the measuring system includes an imaging system configured to in vivo measure a cavity for receiving the object and mapping a receiving surface in the cavity.

In one embodiment, the measuring system includes a sensor system disposed in and operable from at least one of the plurality of passages. The sensor system is configured to ascertain properties of the receiving surface and areas proximate thereto. In one embodiment, the sensor system is configured to ascertain at least one of density, hardness, and chemical composition.

In one embodiment, the positioning of the object comprises forming the object in vivo.

In one embodiment, the positioning of the object comprises forming the object ex vivo.

In one embodiment, one or more segments of the object are formed ex vivo and one or more of the passages has a conveyor system for transporting the segment to the cavity.

In one embodiment, the casing is configured to fit in a lumen of a body.

In one embodiment, the imaging system is a magnetic resonance imaging system, a computed topography system or combinations thereof.

In one embodiment, a coating deployment system disposed in and is operable from one or more of the plurality of passages. The coating deployment system is configured to in vivo apply a biologically engineered substance to the object and/or the receiving surface.

In one embodiment, the multifunctional robotic system employs a biologically engineered substance. For example, the biologically engineered substance is: (a) applied to the object in vivo; (b) applied to the object ex vivo; (c) flowable; (d) injectable; (e) a putty; (f) a paste; (g) a powder; (h) applied to area proximate to the object; (i) forms at least a portion of the object; (j) printable via the printer head; (k) in vivo and ex vivo curable; and (l) combinations thereof. The biologically engineered substance is: (a) a vascularization promoting substance; (b) a growth factor substance; (c) an immune reaction deterrent substance; (d) a bone regeneration substance; (e) a tissue regeneration substance; and 9e) combinations thereof. In one embodiment, the biologically engineered substance is disposed in and applied from the coating deployment system. In one embodiment, the biologically engineered material is a self-assembling arginine-rich peptide that has nanophase characteristics and biomimetic nature and is employed in tissue healing, for example used in an uncured plug form and cured in vivo.

In one embodiment, the printer head includes a material discharge port for in vivo discharging material for in vivo building of the object.

In one embodiment, the object is composed of a plurality of layers of the material formed additively upon one another to establish a predetermined size of the object based upon the properties of the receiving surface and the areas proximate thereto.

In one embodiment, a material removal system is disposed in one or more of the plurality of passages. The object is formed in an oversized state relative to the cavity. The material removal system is configured to establish a predetermined size of the object based upon the properties of the receiving surface and the areas proximate thereto.

In one embodiment, one or more of the passages includes an assembly system and the object has a plurality of segments, each having an interlocking system thereon. The assembly system is configured to in vivo assemble the segments to one another and to lock the interlocking systems of adjacent segments to one another.

In one embodiment, an optical device disposed in and is operable from one or more of the plurality of passages. The optical device is in communication with the computer processor to transmit in vivo images to the computer processor.

In one embodiment, a curing device is disposed in and is operable from one or more of the plurality of passages. The, the curing device is configured to in vivo cure material deposited in a body cavity.

In one embodiment, the curing device is a laser, a heat source, a chemical reactant or combinations thereof.

In one embodiment, a multi-axis positioner is disposed in and is operable from one or more of the plurality of passages. The multi-axis positioner is in communication with the printer head and the computer processor to control dynamic positioning of the printer head in vivo.

In one embodiment, a heat sink, a material evacuation system, a coolant deployment system, an insulation system or combinations thereof is disposed in one or more of the plurality of passages.

In one embodiment, the robotic arm has a sterile interface for mitigating infection caused by in vivo deployment of the object.

In one embodiment, one or more in vivo miniaturized medical devices are in communication with the computer processor.

In one embodiment, an interactive group of in vivo miniaturized medical devices is in communication with the computer processor.

In one embodiment, a post-positioning monitoring system and/or a post-positioning alteration system are in communication with the computer processor. The post-positioning monitoring system is configured to monitor the position of the object relative to the receiving surface and the post-positioning alteration system is configured to reposition and alter the object.

In one embodiment, the measuring system, the sensor system, the post-positioning monitoring system and the post-positioning alteration system is located in the object.

In one embodiment, the printer head, the measuring system, the sensor system, the post-positioning monitoring system and the post-positioning alteration system is located in at least one miniaturized medical device in an in vivo configuration.

There is further disclosed herein, an implant for in vivo deployment. The implant includes a structural member configured for in vivo deployment in a body. The structural member includes a communication system disposed therein. The communications system is configured for communications between the structural member and locations external to the structural member. The implant includes one or more of: (a) an imaging system; (b) a sensor system; and (c) an alteration system, each disposed in the structural member. The imaging system is configured to in vivo measure a cavity for receiving the implant and mapping a receiving surface for the implant and is in communication with the communications system. The sensor system is configured to recognize or ascertain characteristics of the structural member and is in communication with the communication system. The alteration system is configured to alter the characteristics of the structural members and is in communication with the communication system.

In one embodiment, the sensor system includes: (a) a strain sensor configured to measure dimensional changes in the structural member as a function of time; (b) a force sensor configured to measure stresses in the structural member as a function of time; (c) a pressure sensor configured to measure pressure applied to the structural member; (d) an imaging sensor to detect environmental conditions external to the imaging sensor; and (e) combinations thereof.

In one embodiment, the communication system includes a wireless system configured to transmit communication external to the structural member.

In one embodiment, the communication system is in communication with one or more in vivo miniaturized medical devices or is contained in one or more of the in vivo miniaturized medical devices.

In one embodiment, the alteration system includes: (a) a deformation device configured to change dimensions of the structural member to selectively compensate for fit-up anomalies between the structural member and mating surfaces; (b) a tension adjustment device configured to selectively increase and decrease tension in response to external forces applied to the structural member; (c) a density adjustment device configured to selectively adjust density of the structural member; (d) a reactor system configured to selectively dissolve portions of the structural member; (e) one or more in vivo miniaturized medical device in communication with the structural member; and (f) combinations thereof.

In one embodiment, the structural member has outside diameter of a magnitude sufficient to prevent portions of the implant from intruding into trabecular bone of a vertebral body when the structural member is disposed between adjacent vertebral bodies.

In one embodiment, the structural member is made up of a plurality of subsections or segments interlocked with adjacent subsections or segments.

In one embodiment, the structural member is inflatable and deflatable.

In one embodiment, the implant employs a biologically engineered substance. In one embodiment, the biologically engineered substance is: (a) applied to the object in vivo; (b) applied to the object ex vivo; (c) flowable; (d) injectable; (e) a putty; (f) a paste; (g) a powder; (h) applied to area proximate to the object; (i) forms at least a portion of the object; (j) printable via the printer head; (k) in vivo and ex vivo curable; and (l) combinations thereof.

In one embodiment, a portion of or the entire structural member is coated with the biologically engineered substance.

In one embodiment, the biologically engineered substance is one or more of: (a) a vascularization promoting substance; (b) a growth factor substance; (c) an immune reaction deterrent substance; (d) a bone regeneration substance; (e) a tissue regeneration substance; and (f) combinations thereof.

There is also disclosed herein a robotic method for performing in vivo procedures. The method includes providing a control unit that has a computer processor. A robotic arm is in communication with the control unit. The robotic arm has a casing with a plurality of passages therein. A printer head is disposed in one or more of the plurality of passages. An imaging system is disposed in one or more of the plurality of passages. The computer processor is in communication with the printer head and the imaging system. The computer processor has executable software that receives signals from the imaging system. The method includes: (a) in vivo measuring, via the imaging system, a cavity for receiving an object to obtain measurements of the cavity; and/or (b) in vivo mapping, via the imaging system, a receiving surface for receiving the object to obtain a surface map. The executable software analyzes the cavity measurements and/or the surface map, to generate installation parameters. The printer head creates (e.g., in vivo or Ex vivo or combinations thereof) the object based upon the installation parameters. The object is positioned in a predetermined patient specific in vivo location, based upon the installation parameters.

In one embodiment, the method includes providing a sensor system disposed in one or more of the plurality of passages; in vivo ascertaining, via the sensor system, properties of the receiving surface and areas proximate thereto; and the executable software analyzing the cavity measurements, the surface map and the properties of the receiving surface, to generate the installation parameters.

In one embodiment, the method includes ascertaining, via the sensor system, density, hardness and/or chemical composition of the receiving surface and areas proximate thereto.

In one embodiment, the method includes providing a biologically engineered substance. The biologically engineered substance is: (a) applied to the object in vivo; (b) applied to the object ex vivo; (c) flowable; (d) injectable; (e) a putty; (f) a paste; (g) a powder; (h) applied to area proximate to the object; (i) forms a portion of or the entire the object; (j) printable via the printer head; (k) in vivo and ex vivo curable; and (l) combinations thereof.

In one embodiment, the method includes providing a coating deployment system disposed in one or more of the plurality of passages; and the coating deployment system in vivo applies a biologically engineered substance to the object and/or the receiving surface.

In one embodiment, the biologically engineered substance is: (a) a vascularization promoting substance; (b) a growth factor substance; (c) an immune reaction deterrent substance; (d) a bone regeneration substance; (e) a tissue regeneration substance; and (f) combinations thereof. In one embodiment, the biologically engineered substance is disposed in the coating deployment system; and the biologically engineered substance is applied to the object and/or the receiving surface.

In one embodiment, the method includes providing a curing device in one or more of the plurality of passages; and the object is cured in vivo, via the curing device.

In one embodiment, the method includes providing one or more in vivo miniaturized medical devices in communication with the computer processor.

In one embodiment, the method includes providing an interactive group of in vivo miniaturized medical devices in communication with the computer processor.

In one embodiment, the method includes providing a post-positioning monitoring system and/or a post-positioning alteration system, each being in communication with the computer processor. The method includes: monitoring, via the post-positioning monitoring system, positions of the object relative to the receiving surface after in vivo placement of the object; transmitting the positions of the object to the computer processor; evaluating the positions of the object, via the executable software; and determining, via the executable software, the adequacy of the positions of the object. The executable software generates commands to the post-positioning alteration system; and alters the positions of the object based upon the commands.

In one embodiment, the monitoring of the positions, the transmitting of the positions, the evaluating of the positions, the determining of the adequacy of the positions, the generating of the commands and the altering of the positions is accomplished by one or more in vivo miniaturized medical devices.

In one embodiment, the method includes forming one or more segments of the object ex-vivo and transporting the segment into the cavity via one or more of the passages.

In one embodiment, the method includes forming the object via a plurality of layers of the material upon one another to establish a predetermined size of the object based upon the properties of the receiving surface and the areas proximate thereto.

In one embodiment, the method includes providing a material removal system in one or more of the plurality of passages; and forming the object oversized relative to the cavity. The method also includes removing material from the object via the material removal system thereby establishing a predetermined size of the object based upon the properties of the receiving surface and the areas proximate thereto.

In one embodiment, the method includes providing an assembly system in one or more of the passages; and in vivo forming a plurality of segments of the object, each of the segments having an interlocking system thereon. The method includes in vivo assembling the segments to one another using the assembly system.

In one embodiment, the method is employed in one or more of: (a) a medical scaffold positioned between adjacent vertebral bodies, the cavity is located between the adjacent vertebral bodies and the receiving surface is on the adjacent vertebral bodies; (b) in vivo repairing of damaged hard bone or cartilage; (c) in vivo reconstruction of hard bone comprising in vivo reshaping the hard bone by in vivo forming and erecting the medical scaffold on a surface of the hard bone; (d) in vivo repair of a damaged ligament site, comprising imaging the damaged site and determining parameters for a medical scaffold and in vivo forming and erecting the medical scaffold in the damaged site such that the medical scaffold expands and contracts with the ligament and to urge a first torn ligament end towards a second torn ligament end; (e) in vivo repair of soft tissue; and (f) in vivo nerve repair procedures.

In one embodiment, (a) the object is a medical scaffold positioned between adjacent vertebral bodies, the cavity is located between the adjacent vertebral bodies and the receiving surface is on the adjacent vertebral bodies; (b) wherein the method is employed for in vivo repairing of damaged hard bone or cartilage; (c) wherein the method is employed for in vivo reconstruction of hard bone comprising in vivo reshaping the hard bone by in vivo forming and erecting the medical scaffold on a surface of the hard bone; (d) wherein the method is employed for in vivo repair of a damaged ligament site, comprising imaging the damaged site and determining parameters for a medical scaffold and in vivo forming and erecting the medical scaffold in the damaged site such that the medical scaffold expands and contracts with the ligament and to urge a first torn ligament end towards a second torn ligament end; (e) wherein the method is employed for in vivo repair of soft tissue; and/or (f) wherein the method is employed for in vivo nerve repair.

There is disclosed herein a device for in-vivo three-dimensional printing. The device includes a multi-axial robotic arm, a three-dimensional printer head secured to a distal end of the robotic arm; and a control unit in communication with the robotic arm and the three-dimensional printer head. The three-dimensional printer head is configured to coordinate with the control unit to control motion of the robotic arm and operation of the three-dimensional printer head for depositing of material via three-dimensional printing, in-vivo.

In one embodiment, the three-dimensional printer head is configured to print a spacer used in an orthopedic procedure.

In one embodiment, the three-dimensional printer head is configured to print a spacer between two adjacent vertebrae.

In one embodiment, the three-dimensional printer head is configured to print a structure out of polyether-ether-ketone.

In one embodiment, the three-dimensional printer head is configured to print a structure out of titanium alloy.

In one embodiment, the three-dimensional printer head is configured to print a porous object.

In one embodiment, the control unit is in communication with at least one of a magnetic resonance imaging system and a computed tomography system and the control unit is configured to receive a model to be printed that is specific to a patient and is generated by a pre-operative scan performed by at least one of the magnetic resonance imaging system and computed tomography system.

There is also disclosed herein, a method of providing therapy to a patient that includes providing a device for in-vivo three-dimensional printing. The device includes a multi-axial robotic arm, a three-dimensional printer head secured to a distal end of the robotic arm and a control unit in communication with the robotic arm and the three-dimensional printer head. The method includes controlling motion of the robotic arm and the three-dimensional printer head and in-vivo depositing material by the three-dimensional printer head.

In one embodiment, the method includes in-vivo printing a spacer in an orthopedic procedure.

In one embodiment, the method includes in-vivo printing of a spacer between two adjacent vertebrae.

In one embodiment, the method includes in-vivo printing a structure from a polyether-ether-ketone material.

In one embodiment, the method includes in-vivo printing a structure from a titanium alloy.

In one embodiment, the method includes in-vivo printing a porous object.

In one embodiment, the method includes establishing communication between the control unit and at least one of a magnetic resonance imaging system and a computed tomography system, generating a pre-operative scan performed by at least one of the magnetic resonance imaging system and computed tomography system; receiving by the control unit a model to be printed that is specific to a patient.

DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DETAILED DESCRIPTION

Figure 1A:
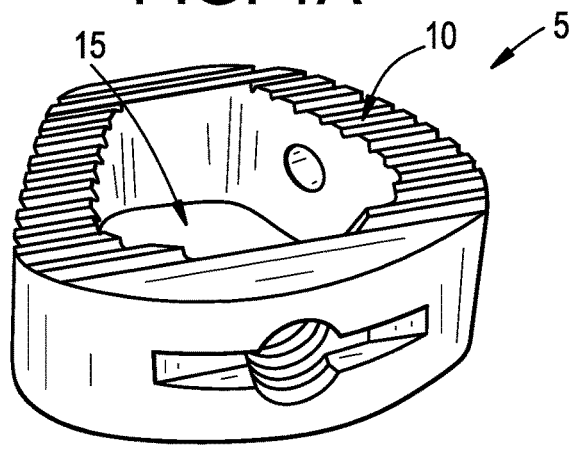
FIG. 1A illustrates a representative anterior cervical spacer formed in accordance with the present invention.
Figure 1B:
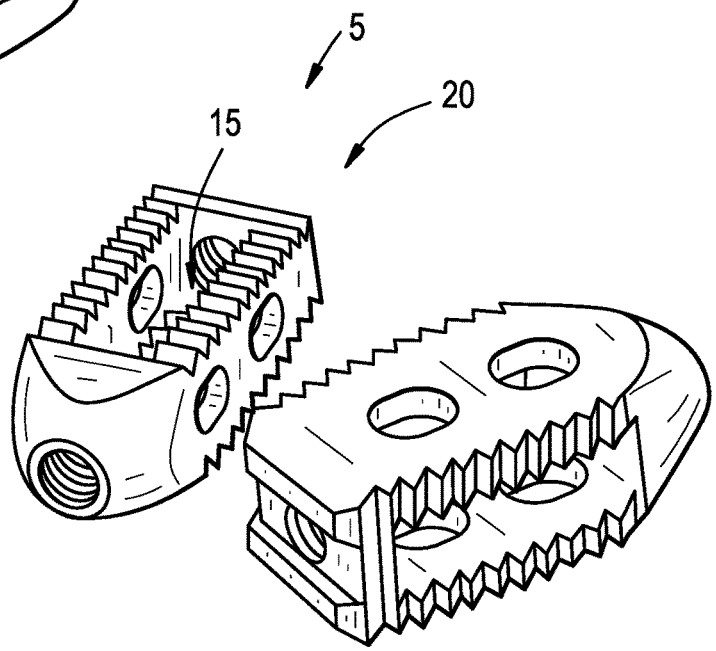
FIG. 1B illustrates a representative posterior lumbar interbody spacer formed in accordance with the present invention.
Figure 1C:
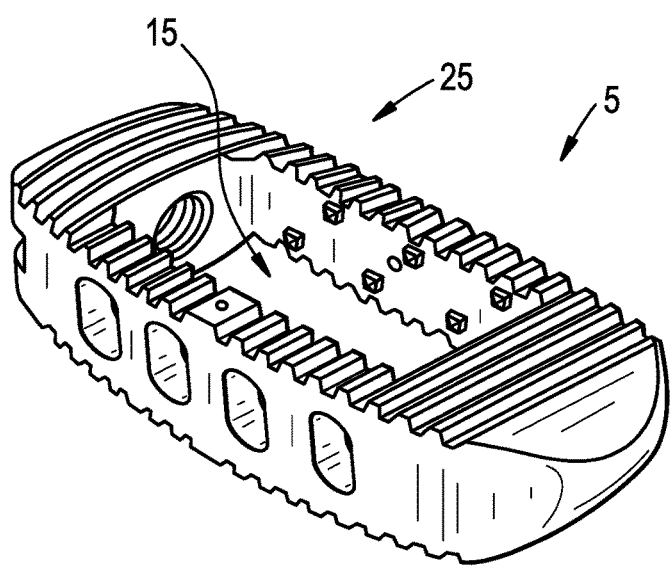
FIG. 1C illustrates a representative transforaminal lumbar interbody spacer formed in accordance with the present invention.

FIGS. 1A-FIG. 1C illustrate exemplary spine spacers 5 used to assist fusion of adjacent vertebrae. FIG. 1A illustrates a cervical spine spacer 10 used to assist in the fusion of adjacent vertebrae. This spacer is used as part of an Anterior Cervical Discectomy Fusion procedure. FIG. 1B illustrates a spacer 20 used for Posterior Lumbar Interbody Fusion. FIG. 1C illustrates a spacer 25 used for Transforaminal Lumbar Interbody Fusion. Spacers 10, 20, and 25 may have a hollow interior region 15 to allow for bone growth. Hollow region 15 may be packed with bone grafting material or other materials known in the art to stimulate bone growth. Spacers 10, 20, and 25 are shown manufactured from PEEK polymers; however, it should be appreciated that these implants may be manufactured from other suitable biocompatible materials including, but not limited to, titanium alloys.

Figure 2A:
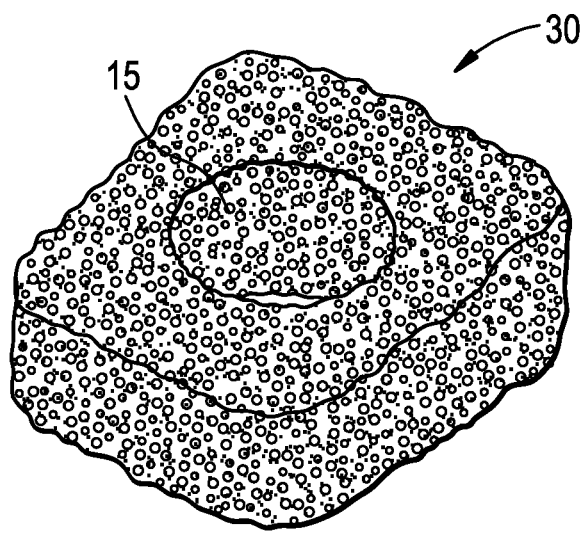
FIG. 2A illustrates a representative Cotton wedge spacer formed in accordance with the present invention.
Figure 2B:
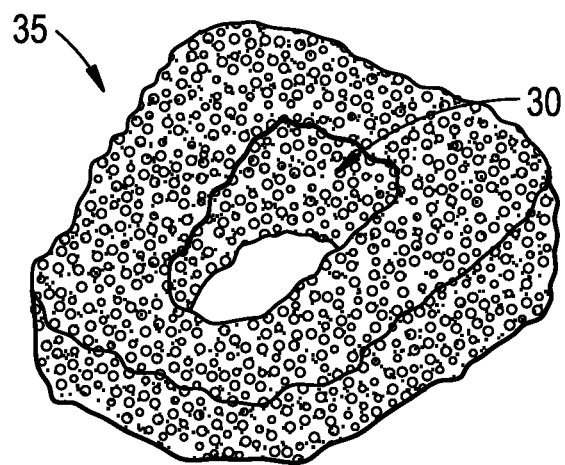
FIG. 2B illustrates a representative Evans wedge spacer formed in accordance with the present invention.

FIG. 2A and FIG. 2B illustrate exemplary spacers used for orthopedic extremity surgery. FIG. 2A illustrates a spacer 30 referred to as a Cotton wedge that is used for osteotomies of the medial cuneiform. FIG. 2B illustrates a spacer 35 referred to as an Evans wedge that is used for lengthening osteotomies of the metatarsals. Spacers 30 and 35 may have a hollow interior region 15 to allow for bone growth. Hollow region 15 may be packed with bone grafting material or other materials known in the art to stimulate bone growth. Spacers 30 and 35 are shown manufactured from a porous titanium alloy; however, it should be appreciated that these implants may be manufactured from other suitable biocompatible materials.

Figure 3A:
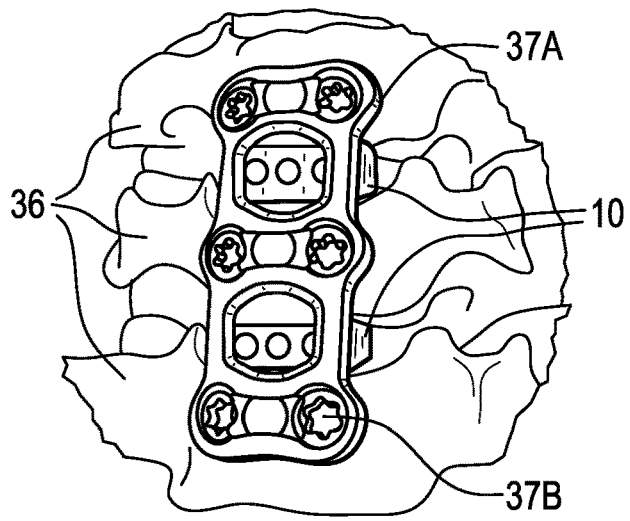
FIG. 3A illustrates a representative Anterior Cervical Discectomy and Fusion implant configuration.
Figure 3B:
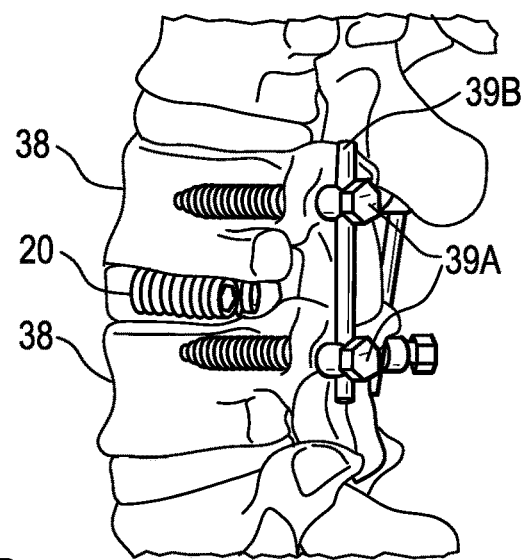
FIG. 3B illustrates a representative Posterior Lateral Interbody Fusion implant configuration.
Figure 3C:
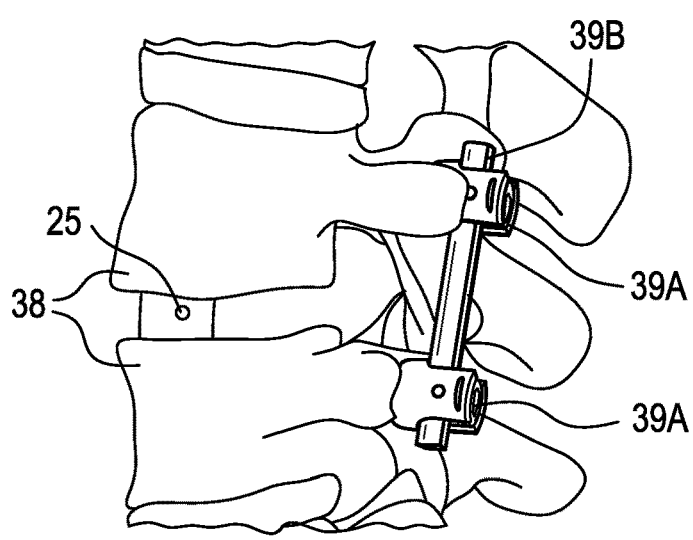
FIG. 3C illustrates a representative Transforaminal Interbody Fusion implant configuration.

FIG. 3A illustrates a representative anterior cervical discectomy and fusion implant configuration. Two spacers 10 are used to maintain vertebral spacing and assist with the fusion of adjacent vertebrae 36 of the cervical spine. A plate 37A may be used to secure the vertebrae in place and create a ridged construct to allow for bone fusion to occur. Plate 37A is fixed to vertebrae 36 using screws 37B. FIG. 3B illustrates a representative posterior lumbar interbody fusion procedure. Two spacers 20 are used to maintain vertebral spacing and assist with the fusion of the adjacent vertebrae 38 of the lumbar spine. Pedicle screws 39A and rods 39B are used to stiffen the construct. FIG. 3C illustrates a representative transforaminal lumbar interbody fusion procedure. A spacer 25 is used to maintain vertebral spacing and assist with the fusion of the adjacent vertebrae 38 of the lumbar spine. Pedicle screws 39A and rods 39B are used to stiffen the construct. Screws and rods shown can be 3D printed or supplement a 3D printed scaffold using off-the-shelf screws and rods.

Figure 4A:
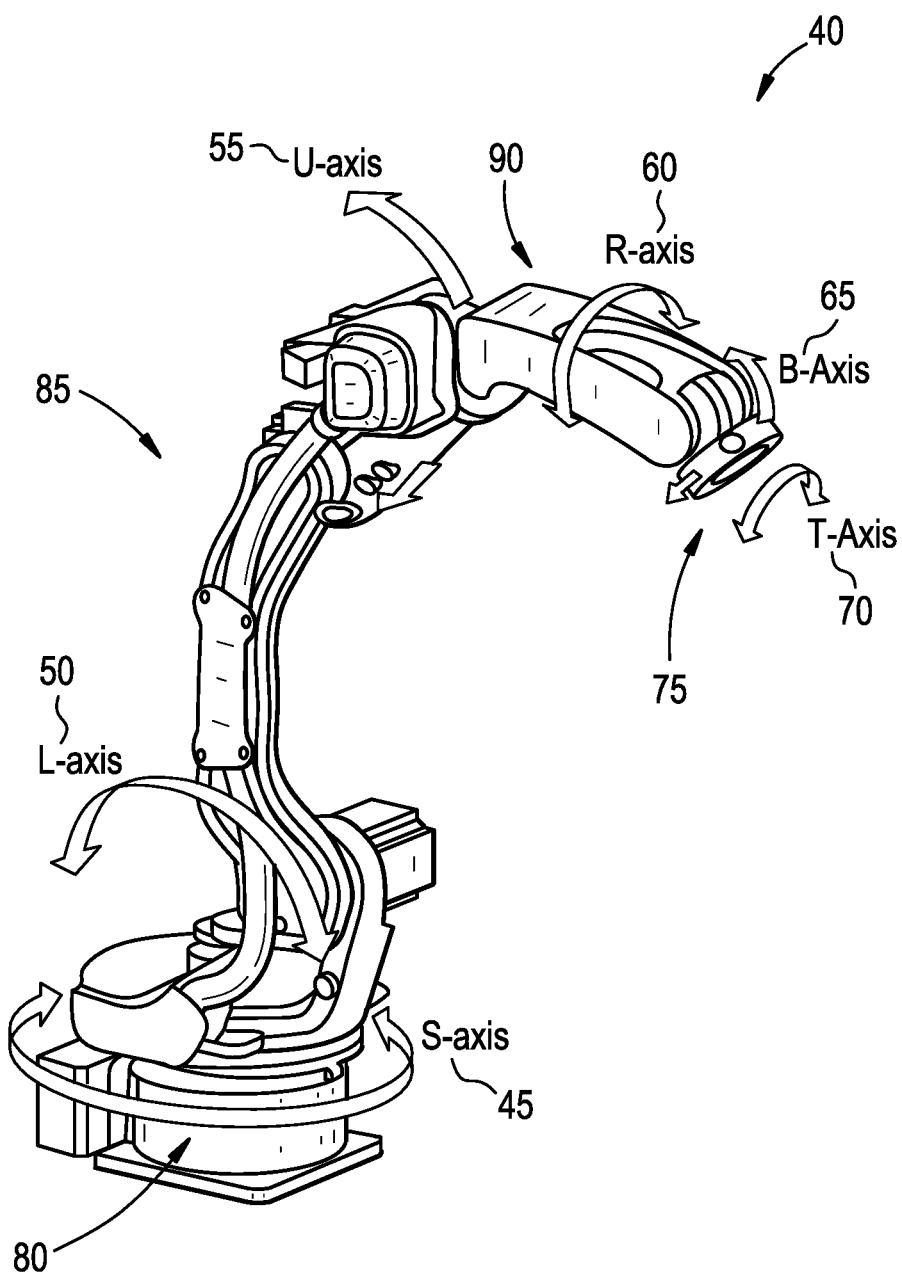
FIG. 4A illustrates a representative robotic arm formed in accordance with the present invention.

FIG. 4A illustrates an exemplary robotic arm 40 that can be used to control a 3D printer head. This robotic arm 40 can be configured to be deployed via an endoscope. Unlike a traditional 3D printer which is limited in motion to the three-basic x, y, and z axes, robotic arm 40 may have many axes to allow the robot to have sufficient degrees of freedom to access the regions needed to print an object such as a spacer, scaffold or implant.

Robotic arm 40 may be a 6-axis robotic arm. S-axis 45 also known as the Fanuc J1 axis is located at the robot base 80 and allows the robot arm to rotate from the left to the right. This motion extends the work area to include the area on either side and behind the arm, thus allowing the arm to be positioned in many positions around the patient. This axis may allow the robot to spin up to a full revolution upon its center point. The L-axis allows the lower arm 85 of the robot to extend forward and backward. It is the axis powering the movement of the entire lower arm. This axis is also known as the Fanuc J2 axis. The U-axis 55 extends the robot's vertical reach. It allows the upper arm 90 to reach behind the body, further expanding the work envelope. This axis gives the upper arm 90 better access to regions of the anatomy and is also referred to as the Fanuc J3 axis. The R-axis 60 works in conjunction with the B-axis 65 to aid in the positioning of the end effector (in this example a 3D printer head). This axis, known as the wrist roll, rotates the upper arm 90 in a circular motion. This axis is also known as the Fanuc J4 axis. The B-axis 65 allows the wrist 70 to tilt up and down. This axis is responsible for pitch and yaw motion. This axis is also known as the Fanuc J5 axis. The T-axis 70 is the wrist of the robot arm. It is responsible for a twisting motion, allowing the robot to rotate freely in a circular motion. It is also known as the Fanuc J6. Attached to T-axis 70 is a mounting plate 75 for attaching a 3D printer head 95 (FIG. 5).

Figure 4B:
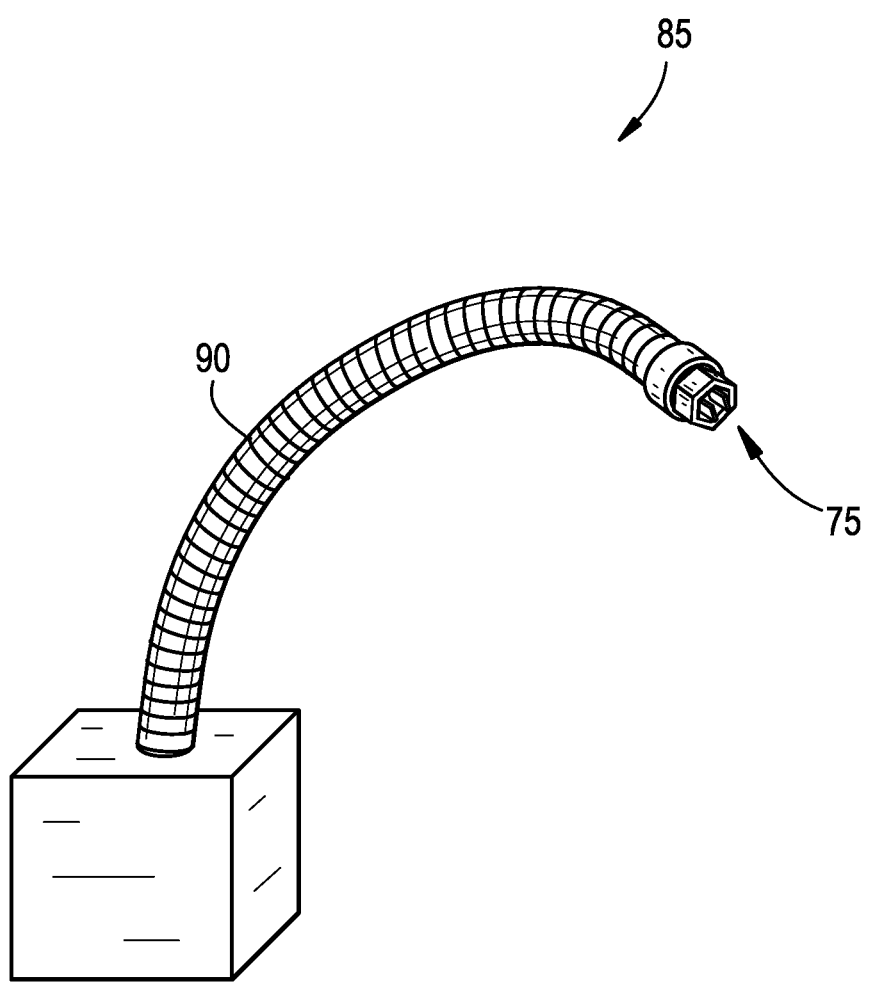
FIG. 4B illustrates a representative robotic arm formed in accordance with the present invention.

Alternatively, FIG. 4B illustrates an exemplary flexible robotic arm 85. Flexible robotic arm 85 is made up of many individual joints 90 that each allow for multiple degrees of freedom. Robotic arm 85 may be attached to a base 80 and has a mount 75 at the end for attachment of a 3D printer head 95 (FIG. 5). A control unit (e.g., the control unit 210 of FIG. 9) is in communication with the robotic arm 85 and the 3d printer head 95 to enable accurate positioning and functionality thereof.

Figure 5:
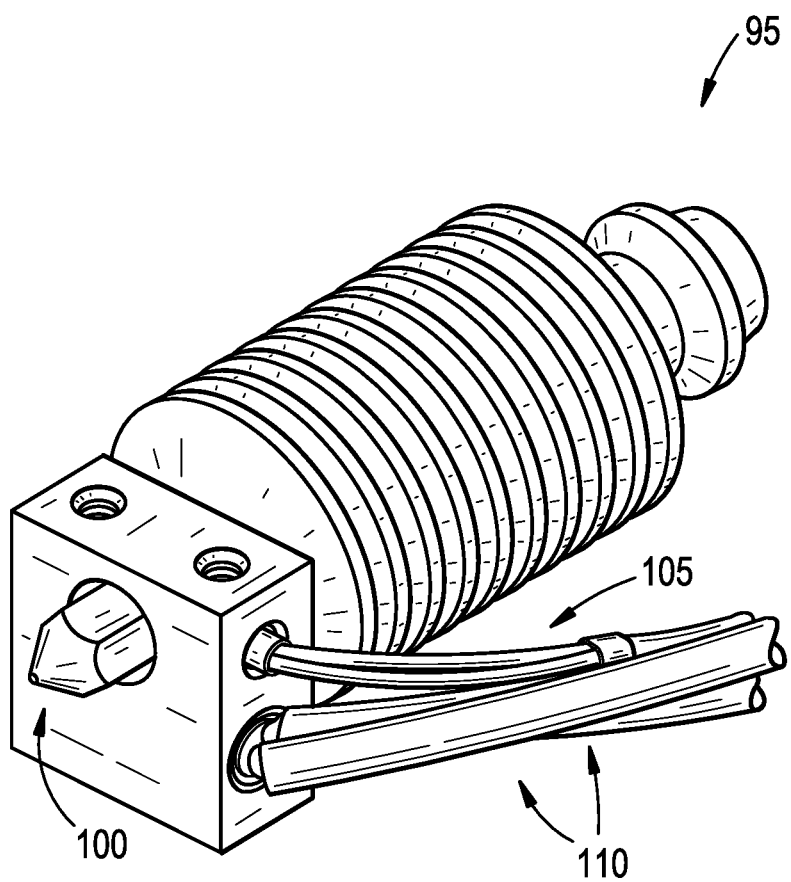
FIG. 5 illustrates a representative 3D printer head formed in accordance with the present invention.

FIG. 5 illustrates an exemplary printer head 95. Printer head 95 has an orifice 100 for extruding material for printing. Material feed line 105 transports raw material to the printer head for use in printing. There may be additional lines 110 for controlling the printer head and providing cooling to the printed part.

Printer head 95 may be compatible with any of the following 3D printing technologies: stereolithography (SLA), digital light processing (DLP), fused deposition modeling (FDM), selective laser sintering (SLS), selective laser melting (SLM), electronic beam melting (EBM), laminated objected manufacturing (LOM). In summary these technologies print material in layers by fusing multiple thin layers atop each other to build structures. The 3D printed object can be fully solid, fully porous, or may have regions of both solid and porous construction.

Many different polymers, metal alloys, ceramics, and composites can be 3D printed using these printing technologies. Suitable polymers include: polyaryl-ether-ketone (PAEK), polyether-ether-ketone (PEEK), poly(glycolic acid) (PGA), and Poly(lactic acid) (PLA). Additionally, many different metal alloys can be 3D printed using these technologies. Suitable metal alloys include: titanium 6-aluminum 4-vanadium (Ti-6-4), commercially pure Titanium (CP-Ti), Cobalt-Chrome-Molybdenum (CoCrMo), and 316 Stainless Steel (316SS). Suitable ceramics include aluminum oxide materials, and calcium phosphate materials (including tricalcium phosphate, calcium hydroxyapatite, etc.). Suitable composites include carbon fiber materials. It should be appreciated that these represent exemplarily biocompatible materials and are not meant to be an exhaustive list of all compatible materials. Depending on the material being printed, the extrusion nozzle may heat the material sufficiently to make it printable. This may be accomplished with thermal resistive heating or ultrasonic energy. For metal alloys (and a subset of polymers) a laser may be used to heat and fuse the material together. Additionally, light curing polymers may be utilized for 3D printing. When utilizing a light curing polymer, the printer head has both a light source of sufficient wavelength and power to cure the polymer, and an orifice for extruding the light curing polymer.

Figure 6:
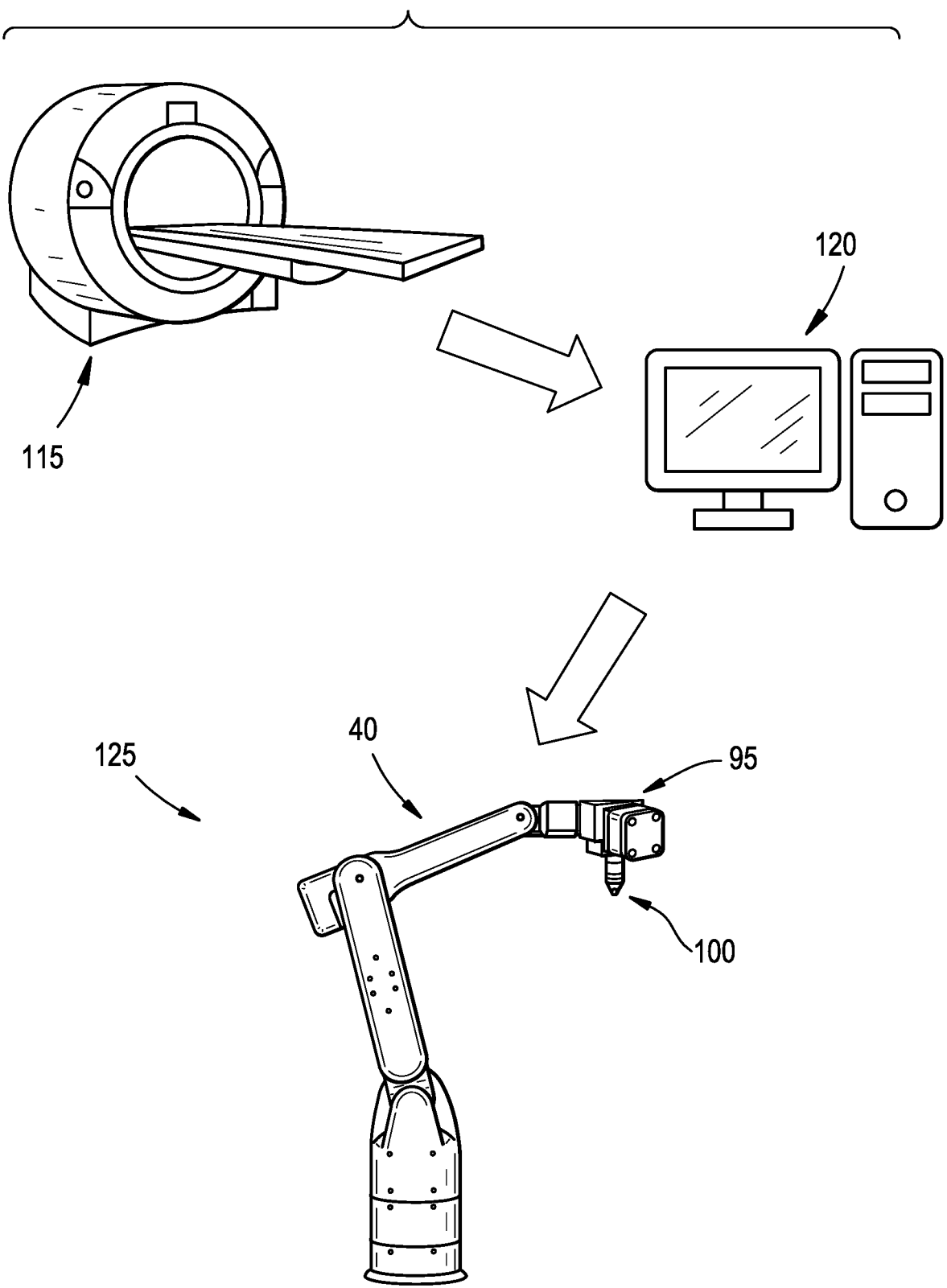
FIG. 6 illustrates a representative workflow for an in-vivo robotic 3D printer formed in accordance with the present invention.

FIG. 6 illustrates a representative workflow for in-vivo robotic 3D printing. Prior to surgery, the patient may undergo a pre-operative CT/MRI scan 115 to produce a computer model of the anatomy including the diseased or damaged tissue. This computer model can be run through a computer 120 which accounts for the patient's age, height, weight, adjacent anatomy, and other physiology to produce a surgery plan and 3D computer model of the object that will be printed. This model is then sent to the robotic 3D printer 125 for printing.

Figure 7:
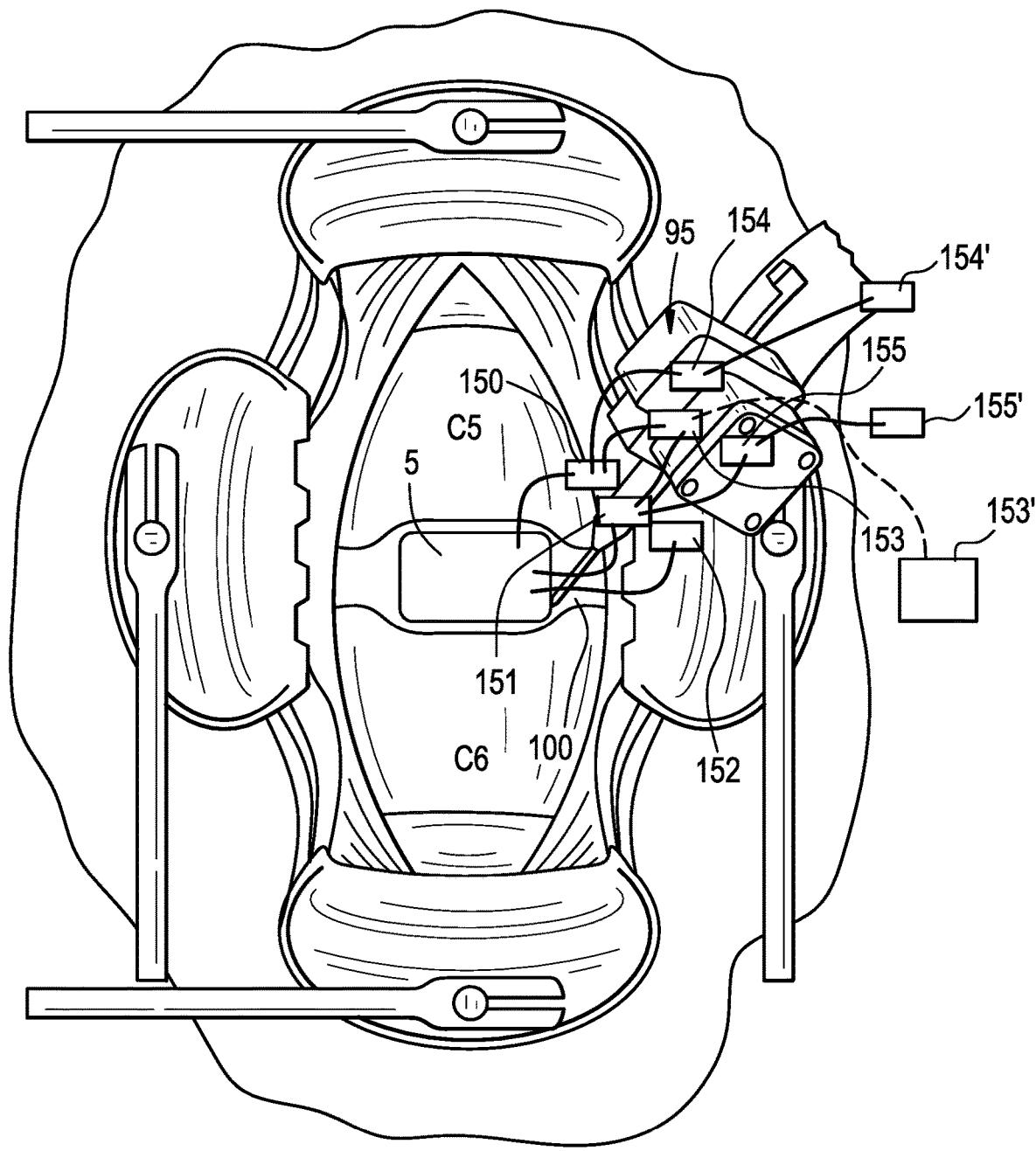
FIG. 7 illustrates a representative in-vivo robotic 3D printer printing a spacer between two adjacent vertebrae.

FIG. 7 illustrates robotic in-vivo 3D printing for a cervical spacer for use in an anterior cervical discectomy fusion. In this procedure an incision is first created to expose the intervertebral disc space. The degenerative disc material is removed, and a burr is used to prepare the endplates of the vertebrae for the spacer. It should be appreciated that the process of exposing the intervertebral disc space and removing the degenerative disc material can be accomplished using the robotic arm and appropriate accessory devices (i.e., scalpel, high speed burr). With the degenerative disc removed, and the endplates prepared, the robotic 3D printer can print the patient specific spacer 5 directly between the two vertebrae.

As shown in FIG. 7, the system for creating orthopedic implants in-vivo during a surgical procedure includes a heat dissipation system 150 and byproduct and waste removal system 151 that are in communication with the head 95, the orifice 100 and/or the object such as spacer 5. The heat dissipation system 150 and the byproduct and waste removal system 151 are in communication with one or more heat exchangers 154, 154' and storage systems 155, 155' located in the head 95 or outside of the body for controlling the temperature of the spacer 5 and surrounding bone and tissue and discharging or adding heat as required. The byproduct and waste removal system 151 is configured to discharge waste generated during the printing process and can be used to supply materials to the print area. The system for creating orthopedic implants in-vivo during a surgical procedure further includes imaging system 152 for measuring the size, hardness, shape of the implants (e.g., spacer 5) in real time as they are being formed and after they cure, as well recording images of the implants and transmitting such images and measurements, in some cases, in real-time to a computer processor 153, 153' located in the head 95 and/or outside of the body.

Figure 8:
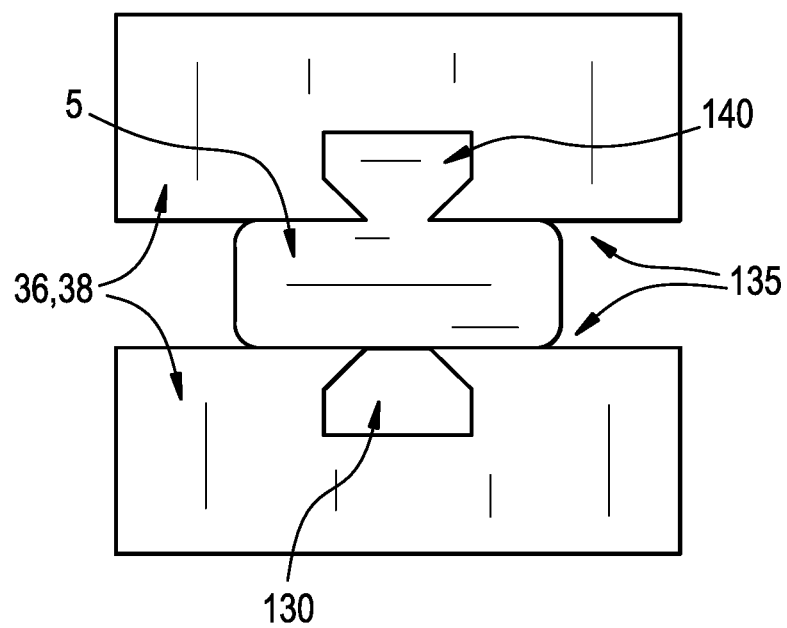
FIG. 8 illustrates a representative keying mechanism to secure a spacer to bone.

It should be appreciated that while the endplates of the vertebrae are being prepared, groves, holes, or other mechanisms for keying the spacer between the vertebrae can be produced. FIG. 8 illustrates a representative keying mechanism for securing spacer 5 to adjacent vertebrae 36, 38. Prior to commencing 3D printing a negative keying mechanism 130 can be cut into the end plates 135. When the spacer 5 is printed, a positive key 140 is printed to fill the negative keying mechanism 130. Thus, when the spacer is printed, it is securely engaged within both vertebrae.

Figure 9:
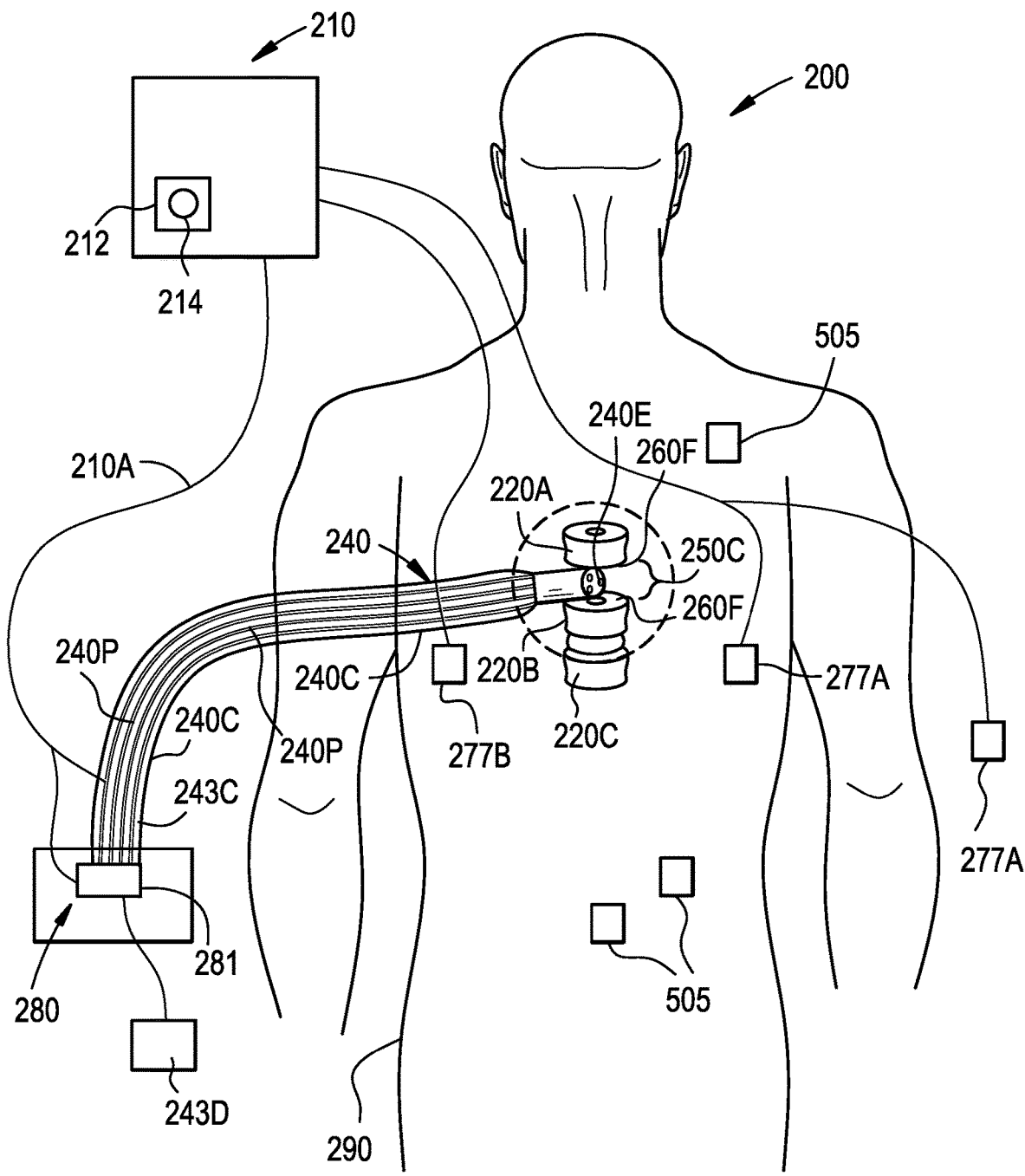
FIG. 9 is a schematic diagram of the multifunction robotic system of the present invention.

As shown in FIG. 9, a multifunctional robotic system for performing in vivo procedures is generally designated by the numeral 200. The system 200 can be configured to be deployed via an endoscope. The multi-function head 295 is configured to survey a target site and prepare the site accordingly. For example, the multi-function head 295 includes a material evacuation system that is configured to remove material such as damaged or diseased tissue. The multifunctional robotic system 200 employs direct visualization and instant feedback for entire procedure. The clinician cleans disc nucleus space and removes soft bone marrow with a flexible instrument using the direct visualization and feedback. For example, the clinician uses a laser scanner to visualize a cavity to determine cleanliness thereof, to obtain images of the cavity and to determine where the bone is to place deploy the medical scaffold 205, as described herein. Sensors or other tools are used to determine the density of the bone to distinguish which is bone and which is soft bone marrow.

The robotic system 200 includes a control unit 210 that has a computer processor 212 therein. The computer processor 212 is configured with executable software 214, as described herein. The robotic system 200 includes a robotic arm 240 pivotally mounted to a base 280. The base 280 includes a control module 281 that is in communication with the control unit 210 via signal conductors 210A. The robotic arm 240 is configured for multi-axis movement as described herein with respect to FIGS. 4A and 4B. While the multifunctional robotic system 200 is described as being used for in vivo procedures, the present invention is not limited in this regard as the multifunctional robotic system 200 may be employed for ex vivo procedures, a combination of in vivo and ex vivo procedures and in cooperation with one or more miniaturized medical devices 505 as described herein with reference to FIGS. 12A and 12B.

Figure 10A:
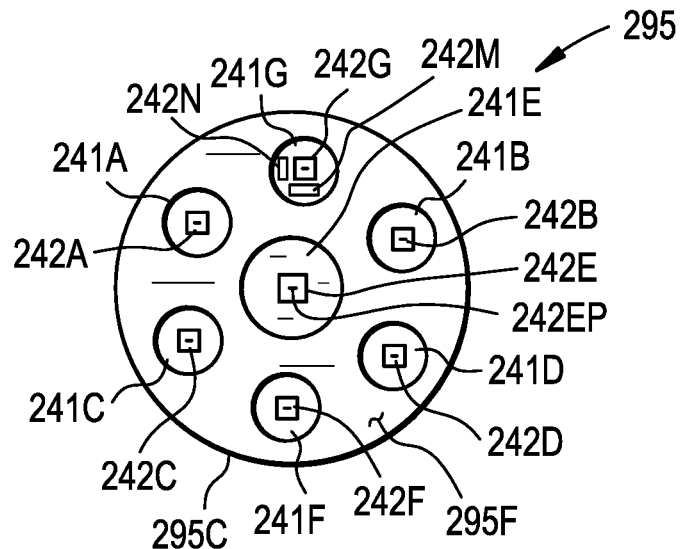
FIG. 10A is an enlarged partial cut away view of detail 10A of FIG. 9.

As shown in FIG. 10A, the robotic arm 240 has a casing 240C that has a plurality of passages 240P therein. The casing 240C is configured to fit in a lumen or tissue, muscle or fat of a body of a living organism, such as a human. As an example, the casing can have a diameter of about 25 mm or less or a diameter such that arm 240 can be deployed to a treatment site via an endoscope.

The passages 240P may be tubular and house electrical conduits, signal cables and sub-tube assemblies. A multifunction head 295 is secured to a distal end of the robotic arm 240. As shown in FIG. 9, the passages 240P are in communication with the control module 281 and the multi-function head 295.

Figure 10B:
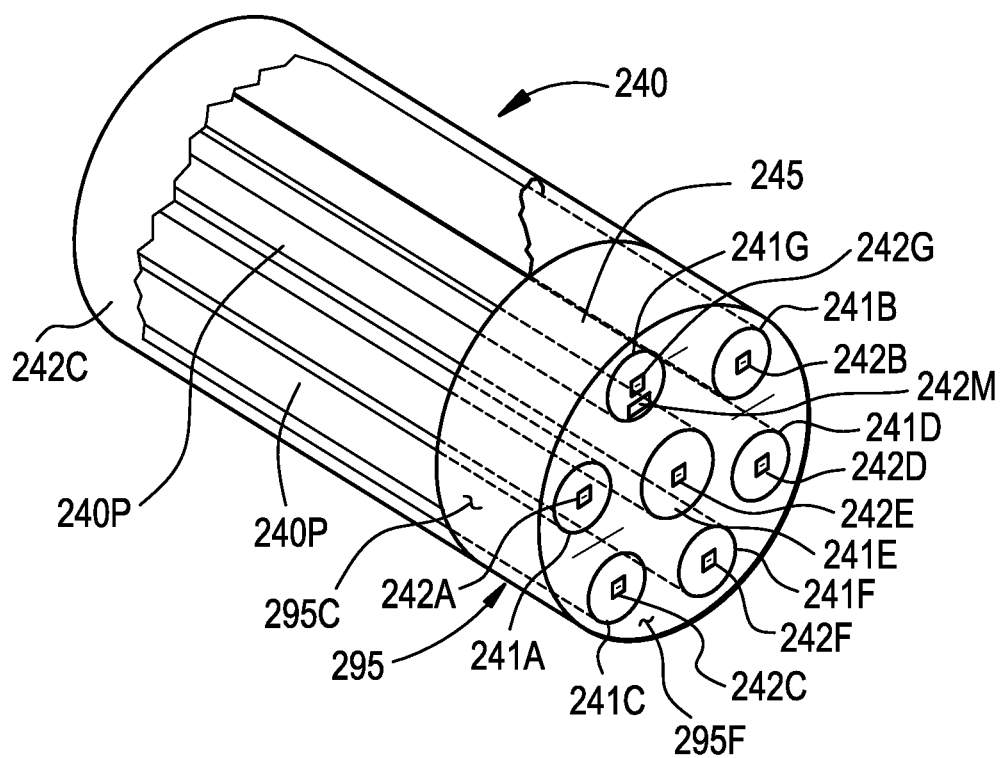
FIG. 10B is a front view of the printer head of FIG. 10A.

As shown in FIGS. 10A and 10B, the multi-function head 295 has seven openings 241A, 241B, 241C, 241D, 241E, 241F and 241G that are in communication with a respective one of the plurality of passages 240P. The openings 241A, 241B, 241C, 241D, 241E, 241F and 241G are illustrated as being on an axial face 295F of the multi-function head 295. However, the openings 241A, 241B, 241C, 241D, 241E, 241F and 241G may be located on other surfaces of the multi-function head 295 such as a circumferential surface 295C of the multi-function head 295 and include more or less than seven openings. While the multi-function head 295 is illustrated as being cylindrical, the present invention is not limited in this regard as other suitable shapes may be employed such as a spherical shape.

As shown in FIGS. 10A and 10B, a printer head 242E is disposed in and is operable from opening 241E of one of the plurality of passages 240P. The printer head 242E is configured to create one or more multi-dimensional objects 205 (e.g., a medical scaffold, an implant, and spacers 5, 10, 20, 25, 30, 35, as described herein with reference to FIGS. 1A, 1B, 1C, 2A and 2B) in vivo, as described herein with reference to the printer head 95 of FIG. 5. The printer head 242E includes a material discharge port 242EP for in vivo discharging a material (e.g., a polymer) for in vivo building of the object 205 (e.g., a medical scaffold).

As shown in FIGS. 10A and 10B, the multifunctional robotic system 200 includes a measuring system that includes an imaging system 242A and/or a sensor system 242B. As shown in FIGS. 10A and 10B, the imaging system 242A is disposed in and is operable from the opening 241A of one of the plurality of passages 240P. The imaging system 242A can be configured to in vivo measure a cavity 250C for receiving the object 205 and mapping a receiving surface 260F of body part 220A, 220B, 220C (e.g., vertebrae), as shown in FIG. 9. For example, the contour and dimensions of the receiving surface 260F including the location of soft and hard tissue, is obtained via the imaging system 242A and is transmitted to the computer processor 212 for analysis by the executable software 214. Images and numerical values of the contour and dimensions are displayed and stored by the computer processor 212. In one embodiment, the imaging system 242A is an optical visualization system. The computer processor 212 includes a display configured to display three-dimensional images of the cavity 250C and the receiving surface 260F and to overlay images of the object 205 to verify proper sizing of the object 205. While the imaging system 242A is described as being an optical visualization system, the present invention is not limited in this regard as a computed topography system, X-ray optics, ultrasonic systems, sonar systems, spectral based imaging systems, and/or magnetic resonance imaging can also be employed.

As shown in FIGS. 10A and 10B, a sensor system 242B is disposed in and is operable from the opening 241B of one of the plurality of passages 240P. The sensor system 242B can be configured to in vivo ascertain properties including density, hardness, anatomy, vibration, force, pressure, temperature and/or, chemical composition of the object and the receiving surface 260F of body part 220A, 220B, 220C and areas proximate thereto.

The computer processor 212 is in communication with the robotic arm, the control module 281, the multi-function head 295, the printer head 242E, the imaging system 242A and the sensor system 242B. The executable software 214 is configured to receive signals from the measuring system, the executable software being configured to control the printer head and the measuring system to position the object in an in vivo location based upon the signals from the measuring system.

As shown in FIGS. 10A and 10B, a coating deployment system 242C is disposed in and is operable from the opening 241C of one of the plurality of passages 140P. The coating deployment system 242C can be configured to store and apply a biologically engineered substance to the object 205 and/or the receiving surface 260F. The biologically engineered substance can be applied to the object 205 in vivo via the coating deployment system 242C (which is either in the opening 241C or in a medical device 505 as described in more detail below). Alternatively, the biologically engineered substance can be applied to the object 205 ex vivo via the coating deployment system 242C or another suitable coating system. In one embodiment, the biologically engineered substance is disposed in and applied to the object 205 from the coating deployment system 242C and it is contemplated that the biologically engineered substance can coat the object 205 or be injected in or around the object 205, e.g., an area proximate to the object. In another embodiment, the object 205 is made from a biologically engineered substance, e.g., is made ex vivo and then implanted in a patient, or 3D printed via the printer head 242E in vivo in a patient.

The biologically engineered substances include, but are not limited to: (a) a vascularization promoting substance; (b) a growth factor substance; (c) an immune reaction deterrent substance; (d) a bone regeneration substance; and (e) a tissue regeneration substance. In some embodiments, the substance comprises a nanomaterial. The biologically engineered substance(s) can be in any form, such as, for example, a putty, a paste, a powder, or a liquid. The biologically engineered substance(s) can be flowable and/or injectable.

Bone regeneration and tissue regeneration substances include, but are not limited to, a composition having polypeptide-functionalized nanotubes capable of encouraging growth and adhesion of certain cells to the object 205. The composition can be flowable or moldable such that it can be placed or positioned in a site or area of choice and then cure into a hardened state. The nanotubes in the composition range in lengths between about 1 nm and about 999 microns, and it is envisioned that the functionality of the nanotubes can vary within the composition, such that different functionalities encourage different cells to grow and adhere to the object 205. Such compositions and nanotubes are described in U.S. Pat. No. 8,795,691, which is incorporated by reference in its entirety herein. It is contemplated that the bone regeneration and tissue regeneration substance can coat an object 205 and/or be injected in or around the object 205 or be the object itself. When the object 205 is made from the bone regeneration and tissue regeneration substance, the substance is capable of being injected or 3D printed and cured in vivo. Alternatively, when the object 205 is made from the bone regeneration and tissue regeneration substance, the object can be formed ex vivo, cured and then implanted in the patient or formed and implanted in vivo.

As shown in FIGS. 10A and 10B, an optical device 242D is disposed in and is operable from the opening 241D of one of the plurality of passages 240P. The optical device 242D is in communication with the computer processor 212 to transmit in vivo images to the computer processor 212. The optical device is configured to have the ability to switch between optical and spectral i.e. Raman spectroscopy to differentiate between different tissues in close proximity to the robotic arm 240.

As shown in FIGS. 10A and 10B, a curing device 242F is disposed in and is operable from the opening 241F of one of the plurality of passages 240P. The curing device 242F is configured to in vivo cure and un-cure material deposited in a body cavity 205. The curing device 242F includes a laser, a heat source and/or a chemical reactant.

Figure 10C:
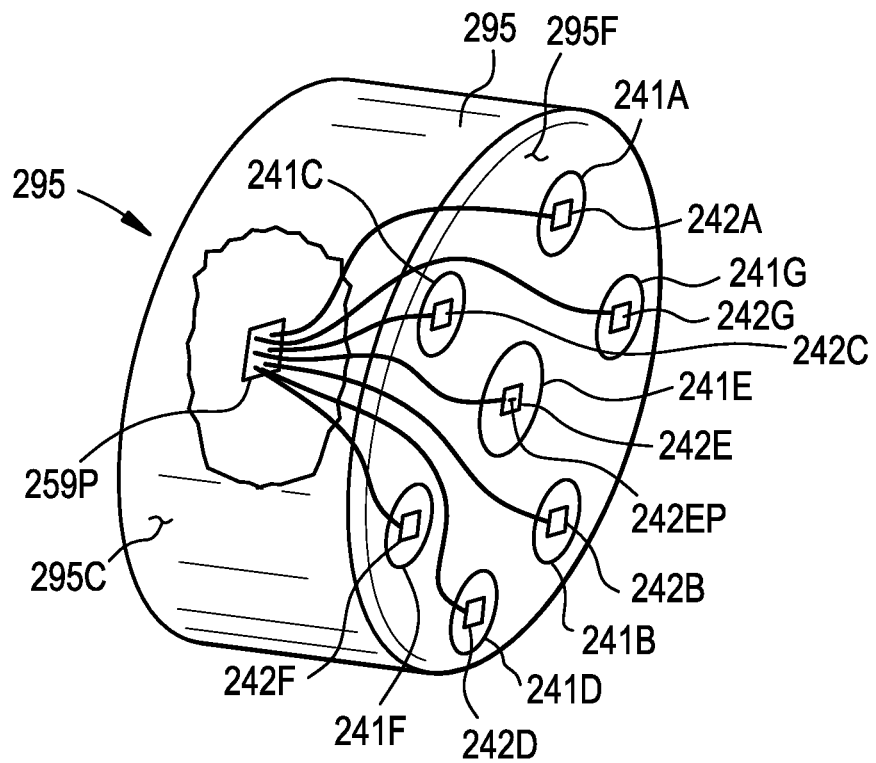
FIG. 10C is an enlarged partial cut away view of the multi-function head of FIG. 10B illustrating a multi-axis positioner.

As shown in FIG. 10C a multi-axis positioner 259P is disposed in the multi-function head 295 and is in communication with imaging system 242A, the sensor system 242B, coating deployment system 242C, the optical device 242D, printer head 242E, the curing device 242F and the computer processor 212 to control and position the imaging system 242A, the sensor system 242B, the coating deployment system 242A, the optical device 242D, printer head 242E (e.g., the dynamic positioning of the print head in vivo) and the curing device 242F, in vivo.

As shown in FIGS. 10A and 10B, the opening 241G includes one or more of a heat sink, a material removal/evacuation system 242M, a coolant deployment system and an insulation system, all of which are in communication with the multi-axis positioner 259P, for control and positioning thereof.

Figure 11:
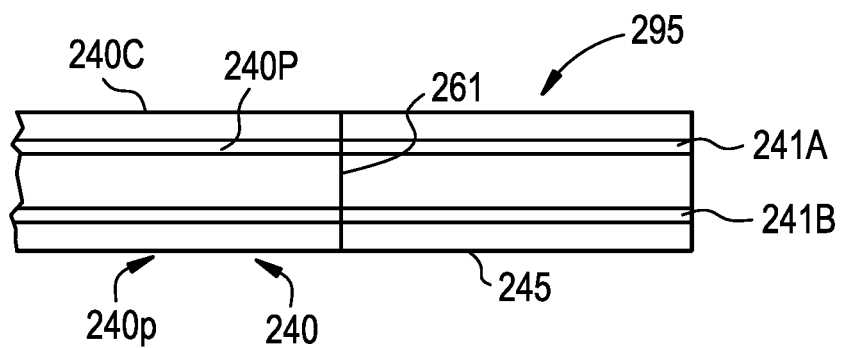
FIG. 11 is a schematic view of the multifunction head of FIG. 10B illustrating a sterile interface.

As shown in FIG. 11, a sterile interface 261 is provided between the robotic arm 240 and the multifunction head 295 for each of the passages 240P, for mitigating infection caused by in vivo deployment of the object 205.

Figure 12A:
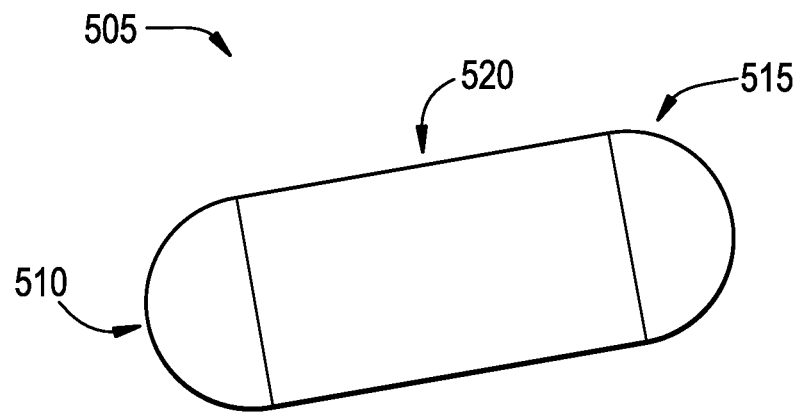
FIG. 12A is a schematic view of a miniaturized robotic medical device.
Figure 12B:
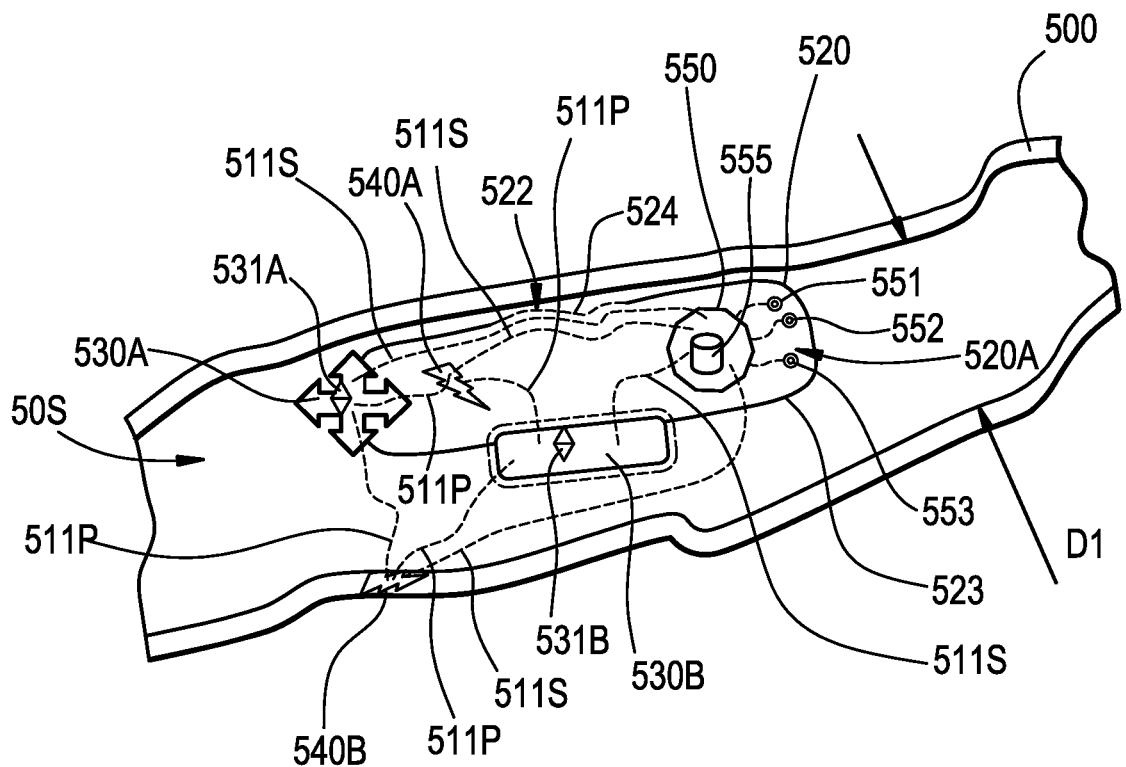
FIG. 12B is a schematic view of the miniaturized robotic medical device of FIG. 12A shown in a lumen of a body.

In one embodiment, and as shown in FIG. 9, a plurality of in vivo miniaturized medical devices 505 are deployed in a lumen of a patient and are used in conjunction with or independent of the multifunctional robotic system 200. In some embodiments, the medical devices 505 can be deployed to perform various functions and subsequently removed via system 200. In some embodiments, the medical devices 505 can remain at the treatment site permanently or semi-permanently, for example, upon reabsorption by the body. In these embodiments, one or more medical devices 505 can be the scaffold itself. Such medical devices 505 are discussed in related PCT Application No. PCT/US2019/24247, incorporated by reference herein. As shown in FIGS. 12A and 12B, an exemplary intra-body controllable medical device (hereinafter "the medical device") 505 is illustrated. In one embodiment, medical device 505 is capsule shaped. Medical device 505 has a distal end 510, a proximal end 515, and body 520 connecting the distal end 510 and proximal end 515. In one embodiment, a control unit, a power supply system, an intra-device storage system, an imaging system, a therapy system, a sample and data gathering system, and a material dispensing system may be located within body 520 of the medical device 505, as described herein. In one embodiment, the medical device 505 works in concert with portions of the multifunctional robotic system 200 by undertaking tasks and functions previously described with respect to the multi-function head 295. For example, in one embodiment the medical device 505 includes in its body 520 one or more of the imaging system 242A, the sensor system 242B, the coating deployment system 242C, the optical device 242D, the printer head 242E, and the curing device 242F. The functions (i.e., measuring, sensing, etc.) not included in the medical device 505 are maintained in the multi-function head 295. In addition to the aforementioned functions, it is further contemplated that the medical device 505 can also perform other functions such as material dispensing or delivery, and sample gathering. The material dispensing or delivery and/or sample gathering can be done in addition to the aforementioned function such that the medical device 505 is multi-functional, or can be done independently of the aforementioned functions, e.g., the multi-function head 295 includes measuring, sensing, etc., while the medical device delivers a pharmaceutical, bone growth material, hardware for installation of an object, etc.

While not illustrated herein, it is contemplated that when a plurality of medical devices 505 are deployed in a patient, the plurality of medical devices includes a combination of two or more of the following: a first medical device having the imaging system 242A, a second medical device having the sensor system 242B, a third medical device having the coating deployment system 242C, a fourth medical device having the optical device 242D, a fifth medical device having the printer head 242E, and a sixth medical device having the curing device 242F. The functions (i.e., measuring, sensing, etc.) not included in the medical device 505 are maintained in the multi-function head 295.

In addition to the aforementioned functions, it is further contemplated that each of the medical devices 505 in the plurality of medical devices can also perform other functions such as material dispensing or delivery and sample gathering. The material dispensing or delivery and sample gathering can be done in addition to the aforementioned functions such that the medical device 505 is multi-functional, or can be done independently of the aforementioned functions, e.g., the multi-function head 295 or one or more other medical devices 505 include measuring, for example, imaging and/or sensing various aspects of the treatment site. In one embodiment, the medical device 505 delivers the biologically engineered substance disclosed herein, a pharmaceutical, bone growth material, hardware for installation of an object, gathers a sample. In one embodiment, the medical device 505 is deployed in vivo by the multifunctional robotic system 200 via the multi-function head 295.

The intra-body controllable medical device 505 is sized according to the anatomy that it will need to navigate, and the method used to deliver it. For example, overall dimensions for medical device operating within the gastrointestinal track may have a diameter of about 25 mm and a length of about 75 mm.

As shown in FIG. 12B, the medical device 505 includes the body 520 having interior area 520A. A first propulsion system 530A and a second propulsion system 530B (e.g., a sprocket and track system) are linked to the host structure 320. While the first propulsion system 530A and a second propulsion system 530B are shown and described, the present invention is not limited in this regard as only one propulsion system or more than two propulsion systems may be employed without departing from the broader aspects of the present invention. The first propulsion system 530A and the second propulsion system 530B are configurable into a peripheral boundary 523 (e.g., a skin or exterior surface) of a miniaturized size and are adapted to fit in a lumen 500 (or tissue, muscle or fat) of a living organism, such as a human. In one embodiment, the medical device 505 is configured to navigate in bone marrow within a bone. In one embodiment, a retractable, removable or pivotable member 524 (e.g., a door, window or flap) selectively covers the opening 522. Propulsion systems 530A and 530B may be used to move device 505 within lumen 500. Additionally, propulsion systems 530A and 530B may be used to as orientation control device 531A and 531B. The propulsion systems can generate smaller and or finer movements to maintain the position of the device within the lumen 500 and can be used to change the orientation of the device within the lumen 500, tissue, muscle or fat. Controlling the orientation of the medical device 505 within the lumen 500, tissue, muscle or fat allows the intra-device storage system, imaging system, therapy system, sample and data gathering system, and/or a material dispensing system to be adjacent to a region of interest within the lumen, tissue, muscle, bone marrow or fat.

As shown in FIG. 12B, a first power supply 540A and a second power supply 540B are in communication (e.g., via power supply conductors or transmission lines or channels generally designated by the dashed lines marked 511P) with the first propulsion system 530A and the second propulsion system 530B. While the first power supply 540A and the second power supply 540B are shown and described as being in communication with the first propulsion system 530A and the second propulsion system 530B, the present invention is not limited in this regard as only one power supply or more than two power supplies may be employed and any of the power supplies (e.g., 530A or 530B) may be in communication with one or more propulsion systems (e.g., 540A or 540B).

As shown in FIG. 12B, a control unit 550 is in communication (e.g., via signal transmitting lines, wires or wireless channels, generally designated by dashed lines marked 511S) with the first propulsion system 530A, the second propulsion system 530B, the first power supply 540A and the second power supply 540B. The control unit 550 includes a computer process controller 555 that is configured to control the first propulsion system 530A, the second propulsion system 530B to move the host structure 520, the first propulsion system 530A and the second propulsion system 530B in the lumen 500 so that the host structure 520, the first propulsion system 530A, the second propulsion system 530B and the control unit 550 are self-maneuverable within the lumen 500.

As shown in FIG. 12B, a tracking device 551, a signal transmitter 552 and a signal receiver 553 are in communication with the control unit 550 via signal lines 511S for tracking and guiding the medical device 505 within the lumen 500.

Figure 13:
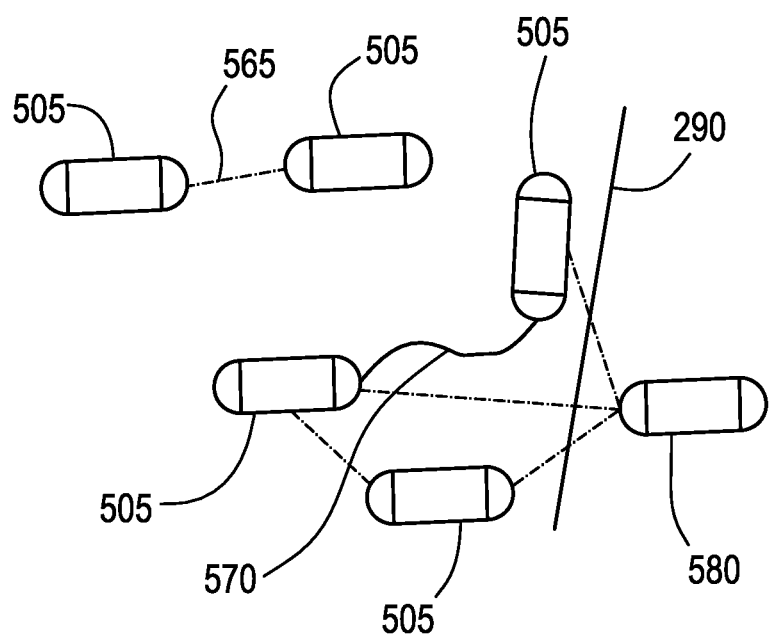
FIG. 13 is a schematic view of an interactive group of the miniaturized robotic medical devices of FIG. 12A.

As shown in FIG. 13, in one embodiment, an interactive group of medical devices 505 in communication with the computer processor 212.

As shown in FIG. 13, the interactive group of devices includes two or more devices 505 that are in communication with one another and/or an external computer-based control system. The two or more medical devices 505 are configured to cooperate with one another to distribute components such as power supplies, medical devices, storage compartments and auxiliary devices among the medical devices so that the medical devices operate together as a group to accomplish the intended functional operations and to enable the use of smaller sized individual medical devices 505 than those that would otherwise not fit into the lumen. The interactive group of medical devices 505 can be configured to operate collectively as a swarm of a plurality of medical devices 505 to provide additional functionality. The interactive group of medical devices 505 includes tethering 570 or towing devices (e.g., winches) between medical devices to assist in propulsion of the medical devices 505 through the lumens. Additionally, the medical devices 505 may communicate wirelessly 565 between devices. Medical devices 505 may communicate with a receiver or controller 580 located outside the body 290. Medical device 505 may operate like a drone, communicating and being controlled by an operator in the same room or in a different location from the patient. Furthermore, when contemplating a swarm of devices, two or more controllable medical devices 505 may be deployed. A first medical device 505 may leave the swarm group and navigate to a region of interest. This device 505 may perform a first task and communicate back to the other devices in the swarm and direct a second device 505 to navigate to the first device 505. Second device 505 may be selected from a number of devices in the swarm because of its particular capabilities (e.g., second device 505 may have an additional battery, an imaging system, a therapy system, a sample and data gathering system, and/or a material dispensing system). Second device 505 may transfer capabilities to first device 505 or second device 505 may perform a task related to its specific capabilities. This serial communication and deployment of devices from the swarm may continue until the desired procedure is completed.

As shown in FIG. 9, a post-positioning monitoring system 277A and a post-positioning alteration system 277B are each in communication with the computer processor 212. In one embodiment, the post-positioning monitoring system 277A is located in vivo (e.g., inside the body 290) and another post-positioning monitoring system 277A is located outside the body 290. It is contemplated that in vivo post-positioning monitoring system 277A and/or the in vivo post-positioning alteration system 227B can be placed in one or more medical devices 505. The post-positioning monitoring systems 277A is configured to monitor the position of the object 205 relative to the receiving surface 260F. The post-positioning alteration system 277B is located in vivo (e.g., inside the body 290) and is configured to reposition and alter the object 205, based upon commands received from the executable software 214.

As shown in the exemplary embodiments illustrated in FIGS. 14A-14G, the imaging system, the sensor system, the post-positioning monitoring system and/or the post-positioning alteration system is located in the object 205, as described herein.

Figure 14A:
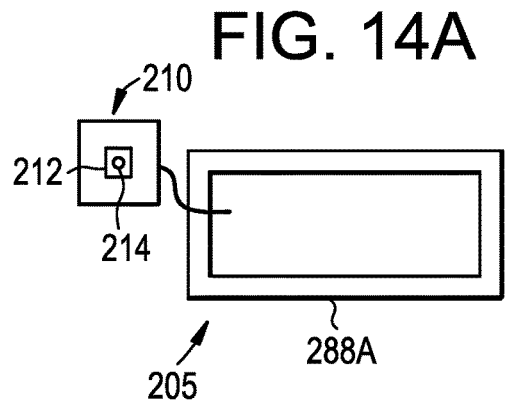
FIG. 14A is a schematic view of a medical scaffold of the present invention illustrated with strain gauges and force sensors.

As shown in FIG. 14A, the object 205 (e.g., the medical scaffold, implant) has a network 288A of strain gauges and force sensors secured thereto, for measuring the fit and changes in fit of the object 205 as a function of time. The network 288A is in communication with the computer processor 212, for transmitting signals and data collected by the network 288A to the computer processor 212. It is contemplated that the network 288A of strain gauges and force sensors is in communication with one or more of the medical devices 505.

Figure 14B:
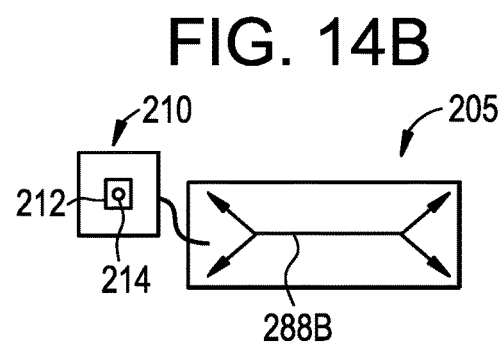
FIG. 14B is a schematic view of a medical scaffold of the present invention illustrated with pressure sensors.

As shown in FIG. 14B, the object 205 (e.g., the medical scaffold, implant) has a network 288B of pressure sensors disposed in (e.g., embedded in) the object 205 for monitoring changes in the external environment surrounding the object 205, such as pressures applied to the object 205 by vertebra 205 (see FIG. 9). The network 288B is in communication with the computer processor 212, for transmitting signals and data collected by the network 288B to the computer processor 212. It is contemplated that the network 288B of pressure sensors can be in communication with one or more of the medical devices 505.

Figure 14C:
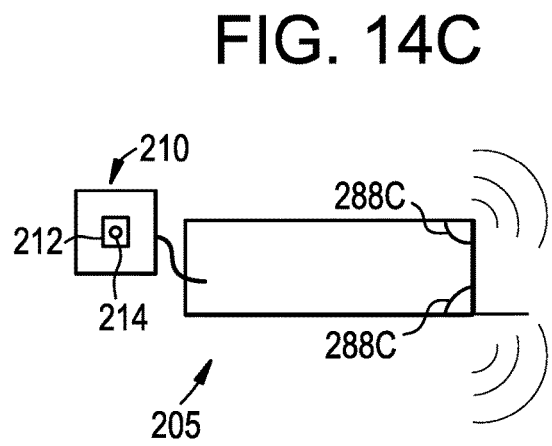
FIG. 14C is a schematic view of a medical scaffold of the present invention illustrated with imaging sensors.

As shown in FIG. 14C, the object 205 (e.g., the medical scaffold, implant) has a network 288C of imaging sensors (e.g., of X-ray radiography, magnetic resonance imaging, medical ultrasonography or ultrasound, confocal microscopy, elastography, optical-coherence tomography, tactile imaging, thermography, spectral imaging, and medical digital photography) disposed in (e.g., embedded in) the object 205 for monitoring changes in the external environment surrounding the object 205. The network 288C is in communication with the computer processor 212, for transmitting signals and data collected by the network 288C to the computer processor 212. It is contemplated that the network 288C of imaging sensors can be in communication with one or more of the medical devices 505.

Figure 14D:
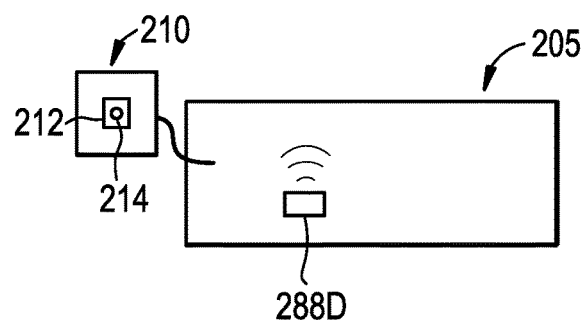
FIG. 14D is a schematic view of a medical scaffold of the present invention illustrated with a wireless communications system.

As shown in FIG. 14D, the object 205 (e.g., the medical scaffold, implant) has a network 288D comprising wireless communications systems (e.g., Bluetooth®, 2G, 3G, 4G, 5G/wife, or any known wireless communication system) disposed in (e.g., embedded in) the object 205 for communication with the computer processor 212 and for transmitting signals and data collected by the network 288C to the computer processor 212. It is contemplated that the network of 288D of imaging sensors can be in communication with one or more of the medical devices 505.

Figure 14E:
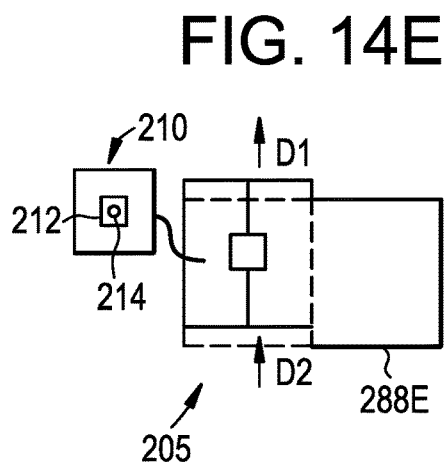
FIG. 14E is a schematic view of a medical scaffold of the present invention illustrated with a device for selectively deforming the medical scaffold.

As shown in FIG. 14E, the object 205 (e.g., the medical scaffold, implant) has a device 288E for selectively deforming the object (e.g., expanding in the direction of the arrow D1 or contracting in the direction of the arrow D2) disposed in (e.g., embedded in) the object 205 for adjusting the fit of the object 205 in the cavity 250C (see FIG. 9). The device 288E is in communication with the computer processor 212, for transmitting signals to the device 288E for selective deformation of the object 205. It is contemplated that the device 288E can be in communication with one or more of the medical devices 505.

Figure 14F:
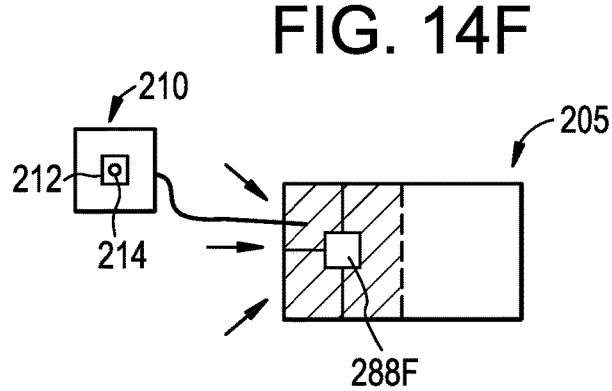
FIG. 14F is a schematic view of a medical scaffold of the present invention illustrated with a device for selectively changing the hardness, composition and/or density of the medical scaffold.

As shown in FIG. 14F, the object 205 (e.g., the medical scaffold, implant) has a device 288F for selectively change the hardness, composition and/or density of the object (e.g., tension or loosen) disposed in (e.g., embedded in) the object 205 for adjusting the fit of the object 205 in the cavity 250C (see FIG. 9). The device 288F is in communication with the computer processor 212, for transmitting signals to the device 288F for selective changing the hardness, composition and/or density of the object 205. It is contemplated that the device 288F can be in communication with one or more of the medical devices 505.

Figure 14G:
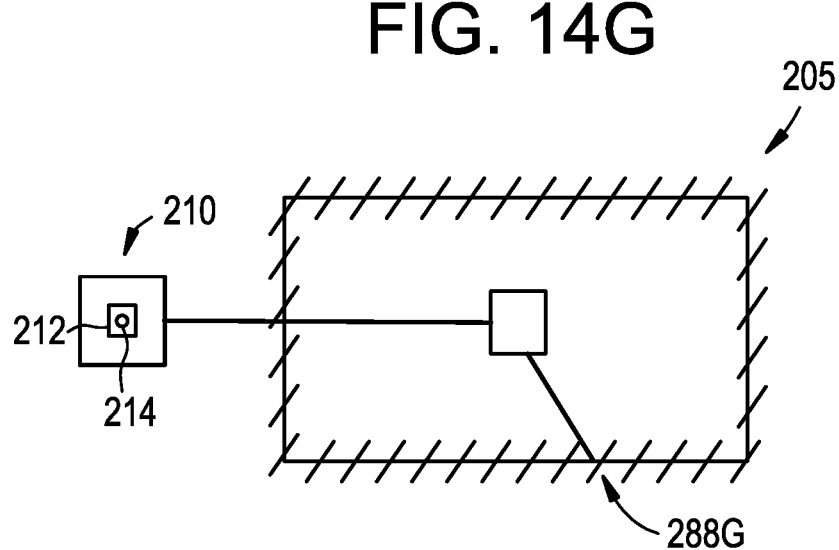
FIG. 14G is a schematic view of a medical scaffold of the present invention illustrated with module configured to selectively dissolve portions of or the entire medical scaffold.

As shown in FIG. 14G, the object 205 (e.g., the medical scaffold, implant) includes a module 288G configured to selectively dissolve portions of or the entire object 205 disposed in (e.g., embedded in) the object 205 for adjusting the fit of the object 205 in the cavity 250C (see FIG. 9). The device 288G is in communication with the computer processor 212, for transmitting signals to the device 288G for the selective deformation of the object. It is contemplated that the module 288G can be in communication with one or more of the medical devices 505.

Figure 14H:
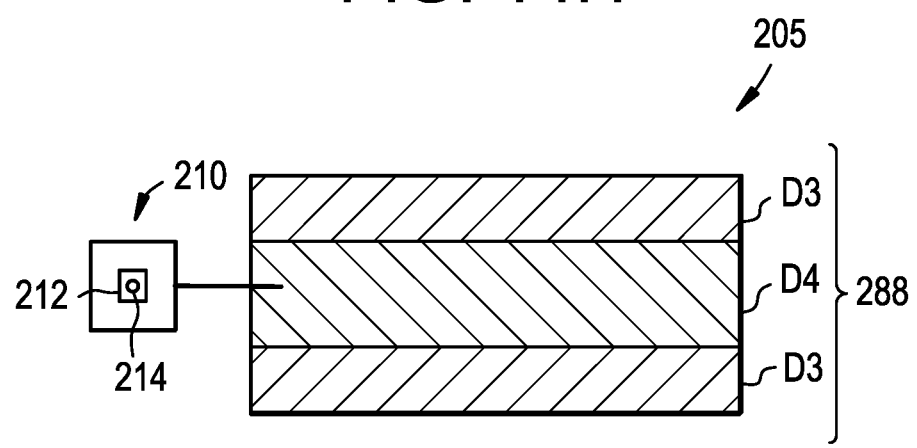
FIG. 14H is a schematic view of a medical scaffold of the present invention illustrated with layers of different densities.

As shown in FIG. 14H, the object 205 includes layers D3 and D4 that have different densities.

As discussed above, in one embodiment the printer head 242E, the imaging system 242A, the sensor system 242B, the post-positioning monitoring system 277A and/or the post-positioning alteration system 277B is or are located in one or more miniaturized medical devices 505 in an in vivo configuration, for example as illustrated in FIGS. 12A, 12B and 13. The post-positioning monitoring systems 277A are deployed after the initial installation of the object 205 in the body 290 to obtain condition parameters indicative of the fit of the object 205 relative to the receiving surfaces 260F and to transmit the condition parameters to the computer processor 212. The executable software analyzes the condition parameters and generates signals to the post-positioning alternation system 277B to implement alterations to the object 205.

Figure 15A:
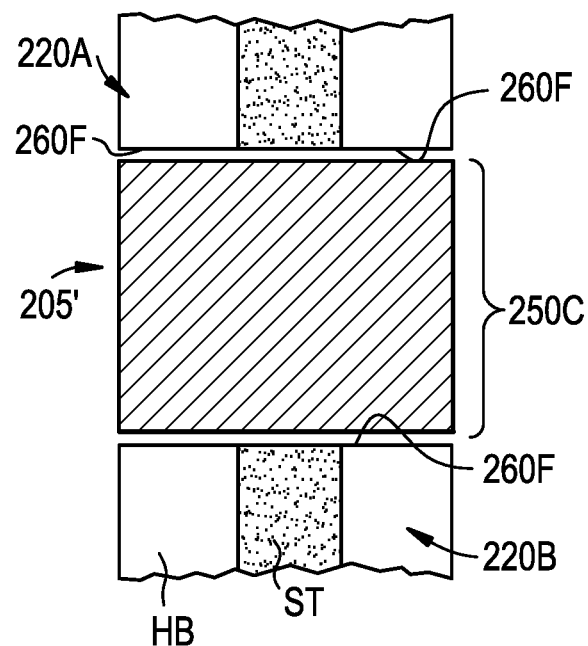
FIG. 15A is a schematic coronal view of the precursor state of the medical scaffold of the present invention shown positioned between two vertebra before sizing.
Figure 15B:
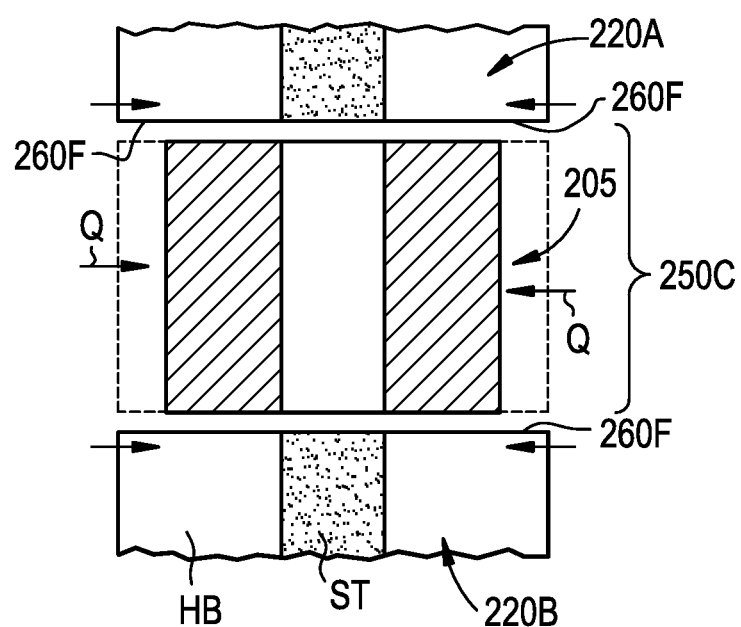
FIG. 15B is a schematic coronal view of the medical scaffold of the present invention shown positioned between two vertebra after sizing.

As shown in FIG. 15A, in one embodiment, the medical scaffold 205 is formed using negative techniques. For example, the medical scaffold 205' is in vivo formed in an oversized condition (e.g., oversized relative to the cavity 250C) in the cavity 250N and/or in an area proximate to the cavity 250C using the printer head 242E to inject material into the cavity 250C or the area proximate thereto. As shown in FIG. 9, the multi-function head 295 includes a material removal system 242M (e.g., a machining system, a scraper, a vacuum, and/or a dissolving system) disposed in one or more openings 241A, 241B, 241C, 241D, 241E, 241F and 241G and/or in one or more of the passages 240P. The material removal system 242M is employed in vivo to remove material from the oversized medical scaffold 205' to create a predetermined and properly sized medical scaffold 205 based upon the properties of the receiving surface 260F and the areas proximate thereto, as shown in FIG. 15B. The material removed from the oversized medical scaffold 205' is disposed of via a suction system and/or dissolved in vivo. The properly sized medical scaffold 205 (e.g., implant) is sized to seat on the hard bone HB of the vertebra 220A and be spaced apart from the soft tissue ST of the vertebra 220A, as shown in FIG. 15B. In some embodiments, the medical scaffold 205 can be formed to a size relative to the cavity and subsequently, the material removal system 242M can remove one or more portions of the scaffold 205 to create a pores or voids in scaffold 205. In some embodiments, one or more substances can be injected into the pores or voids, for example, a substance to promote cell adhesion and growth surrounding the scaffold 205.

Figure 15C:
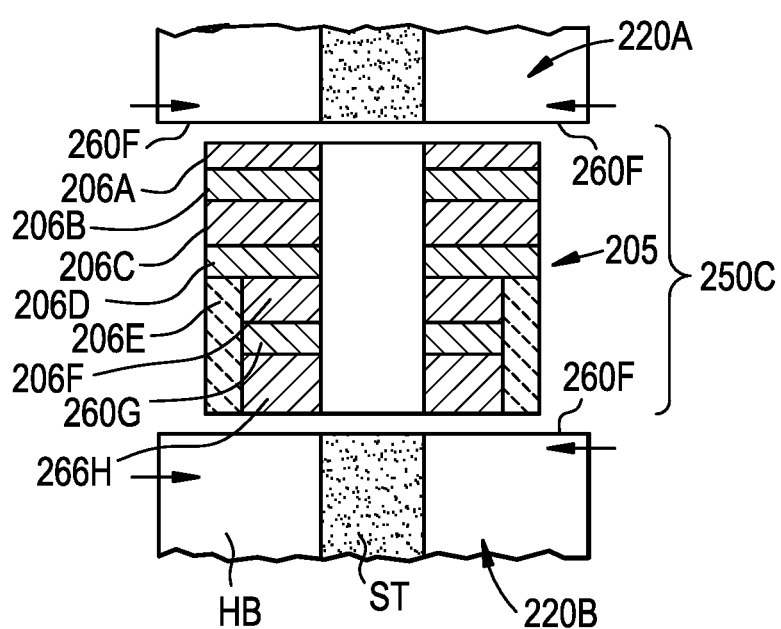
FIG. 15C is a schematic view of a medical scaffold having a plurality of layers, in accordance with aspects of the present disclosure.

As shown in FIG. 15C, the medical scaffold 205 has a plurality of layers 206A, 206B, 206C, 206D, 206E, 206F, 206G and 206H that are formed additively by successively applying the layers 206A, 206B, 206C, 206D, 206E, 206F, 206G and 206H to one another by the printer head 242E in vivo or ex vivo. The layers 206A, 206B, 206C, 206D, 206E, 206F, 206G and 206H are formed axially radially, circumferentially and combinations thereof. The number and size of the layers 206A, 206B, 206C, 206D, 206E, 206F, 206G and 206H are determined by the executable software 214 to create a properly sized medical scaffold 205. The layers 206A, 206B, 206C, 206D, 206E, 206F, 206G and 206H of the material formed additively upon one another establish a predetermined size of the medical scaffold 205 based upon the properties of the receiving surface 260F and the areas proximate thereto.

While the medical scaffold 205 is shown and described as being positioned between the two vertebra 220A and 220B, the present invention is not limited in this regard as the medical scaffold 205 may be positioned in other parts of a body, internally or externally, including but not limited to bone, soft tissue and ligaments.

Figure 16A:
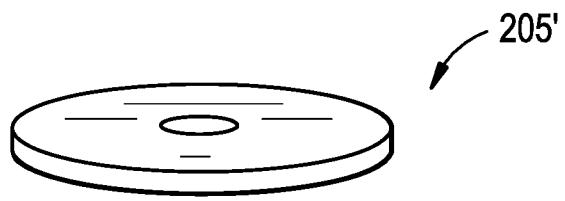
FIG. 16A is a schematic view of an embodiment of the medical scaffold of the present invention shown in a deflated state.
Figure 16B:
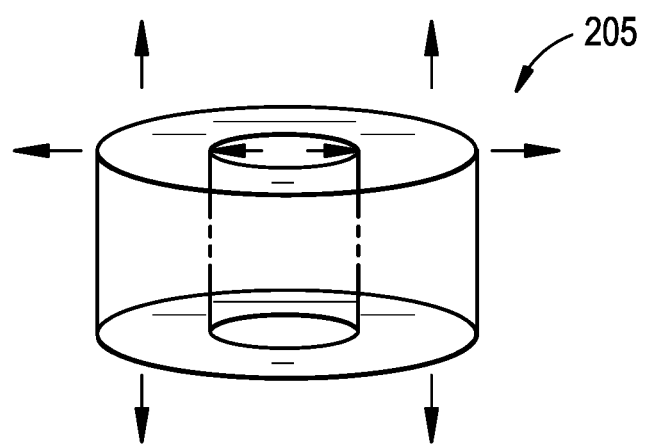
FIG. 16B is a schematic view of the medical scaffold of FIG. 16A shown in an inflated state.

As shown in FIGS. 16A and 16B, the object 205 is selectively inflatable and deflatable by injecting or withdrawing a fluid (e.g., gas, liquid or gel), respectively. A deflated object 205' is illustrated in FIG. 16A and inflated object 205 is shown in FIG. 16B. In the inflated state, the object 205 is properly sized to fit in a predetermined cavity, such as between two adjacent vertebra.

Figure 17A:
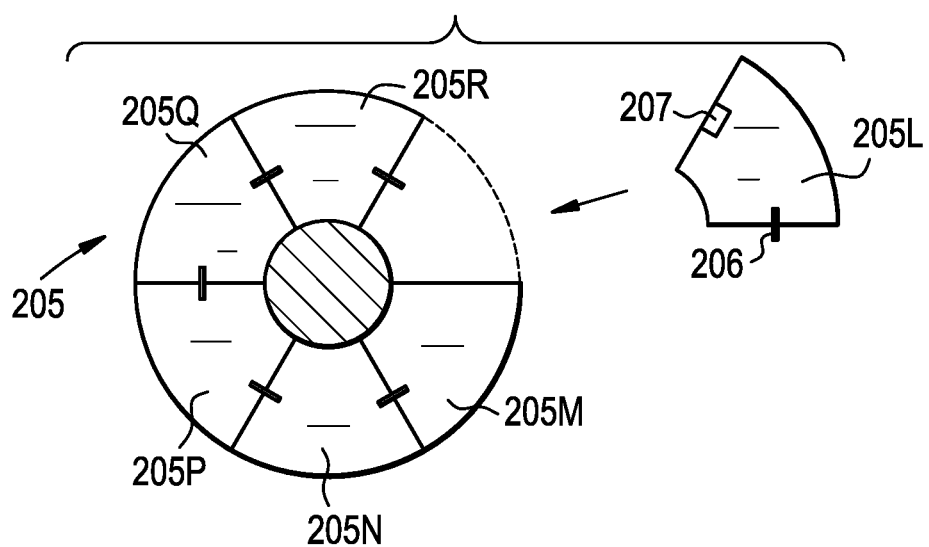
FIG. 17A is an exploded axial view of a segmented medical scaffold of the present invention.
Figure 17B:
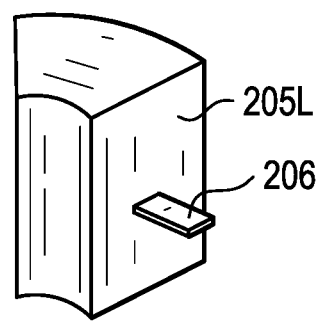
FIG. 17B is a perspective view of one of the segments of the medical device of FIG. 17A showing interlocking features employed therewith.

As shown in FIGS. 17A and 17B the object 205 includes a plurality of subsections or segments 205L, 205M, 205N, 205P, 205Q and 205R that are interlocked with adjacent subsections or segments, via an interlocking system such as latch 206 and slot 207 arrangement. One or more of the passages 240P has an assembly system 242N therein. The assembly system 242N is configured to in vivo assemble the segments 205L, 205M, 205N, 205P, 205Q and 205R to one another and to lock the interlocking systems of adjacent segments 205L, 205M, 205N, 205P, 205Q and 205R to one another. The assembly system 242N is in communication with and receives commands from the executable software 214 to control the assembly process. The segments 205L, 205M, 205N, 205P, 205Q and 205R are formed in vivo via the printer head 242E. In some embodiments, one or more of the segments 205L, 205M, 205N, 205P, 205Q and 205R are formed ex vivo. In some embodiments, one or more of the passages 240P has a conveyor system 243C (see FIG. 9) arranged therein for transporting the segments 205L, 205M, 205N, 205P, 205Q and 205R to the cavity 250C. In one embodiment, the conveyor system 243C includes a fluid pressurization and depressurization source 243D that is in communication with the passage 240P to transport the segments 205L, 205M, 205N, 205P, 205Q and 205R in the passage 240P to the cavity 250C, via a fluid such as a liquid or gas. Mechanical conveyor systems (e.g., lanyards, tracks or magnetic devices) may also be employed to transport the segments 205L, 205M, 205N, 205P, 205Q and 205R in the passage 240P to the cavity 250C.

Figure 18:
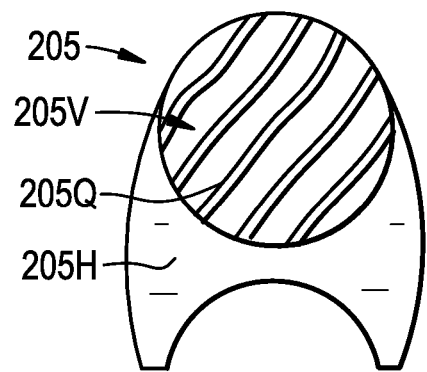
FIG. 18 is a coronal view of the medical scaffold of the present invention shown with solid non-vascularized zone and a vascularized zone.

As shown in FIG. 18 in a meniscus or other cartilage application, the medical scaffold 205 includes a solid portion 205H and a vascularized portion 205V that has a plurality of vascular passages 205Q selectively formed therein.

Figure 19A:
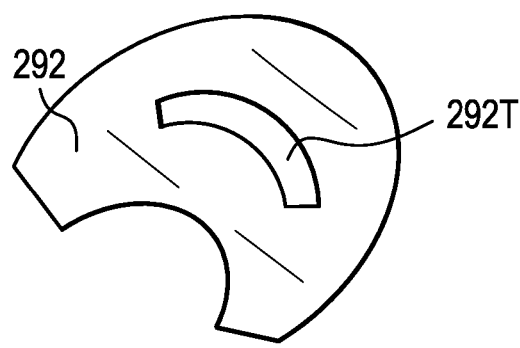
FIG. 19A is an axial view of a ligament with a partial tear therein.
Figure 19B:
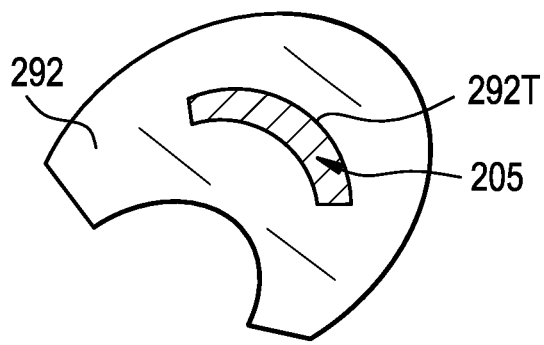
FIG. 19B is an axial view of the ligament of FIG. 19A with a medical scaffold of the present invention disposed in the tear.

As shown in FIG. 19A a cartilage 292 with a partial tear 292T (e.g., meniscus tear) is shown in an axial view. A medical scaffold 205 is shown disposed in the tear 292T. As shown in FIG. 19B, the medical scaffold is shown positioned in a damaged cartilage site. The medical scaffold 205 can be in vivo formed and erected in the damaged site based upon prior imaging and mapping of the damaged site. A biologically engineered substance may be employed to promote vascularization and growth of the cartilage 292.

Figure 19C:
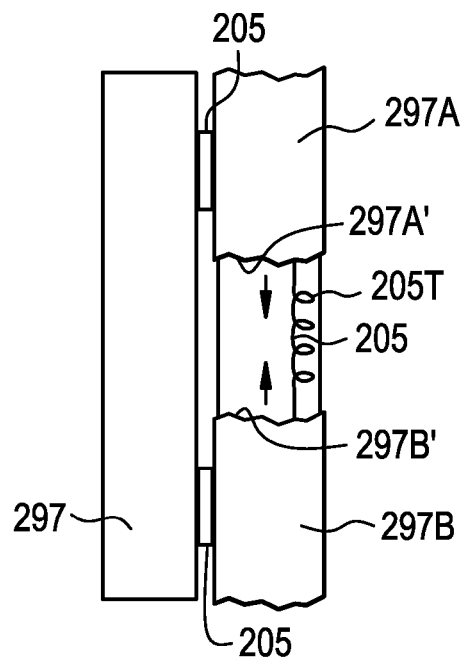
FIG. 19C is a coronal view of the medical scaffold shown disposed in a torn ligament site.

Referring to FIG. 19C, a ligament 297 is shown with a tear (e.g., torn anterior cruciate ligament (ACL) or torn medial patellofemoral ligament (MPFL)) therethrough. The medical scaffold 205 is secured to a first end 297A' of a portion of the torn ligament and is also secured to a second end 297B' of another portion 297B of the torn ligament 297. The medical scaffold 205 includes a tensioner 205T which urges the first torn ligament end 297A' towards a second torn ligament end 297B' to promote curing and healing of the torn ligament. Thus, the medical scaffold 205 deforms, flexes, expands and contracts with the ligament 297. The torn ligament 297 is cross linked with one or more adjacent health ligaments 297 and tissue via one or more of the medical scaffolds 205. A biologically engineered substance may be employed to promote vascularization and growth of the ligament 297.

Figure 20:
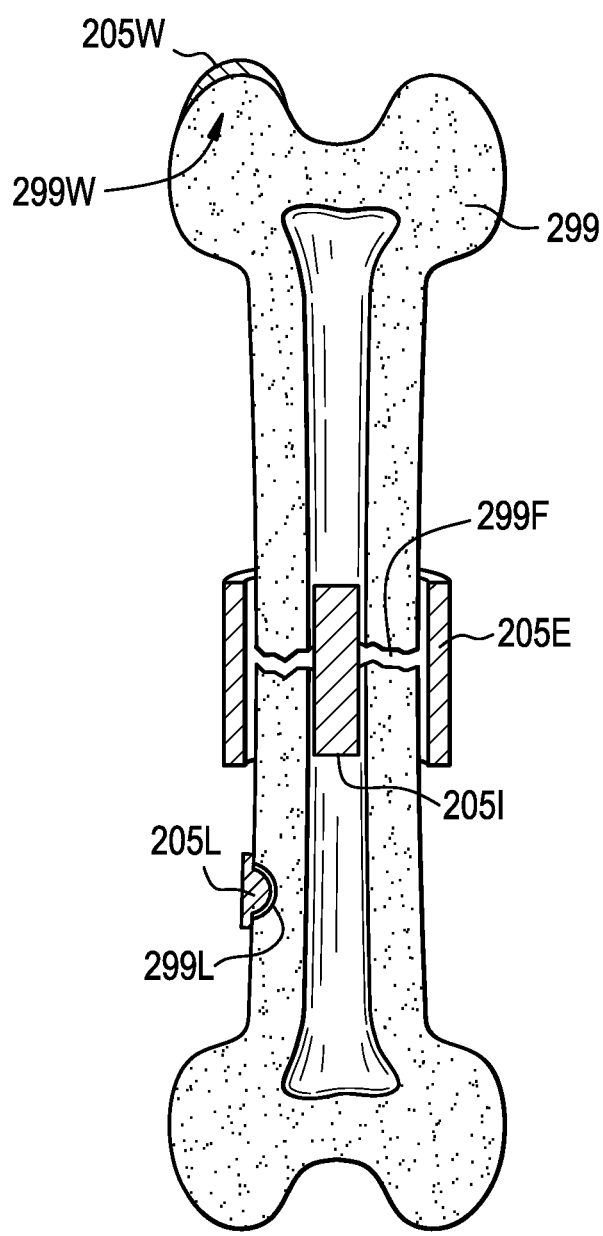
FIG. 20 is a schematic view of a fractured bone have medical scaffolds deployed thereon.

As shown in FIG. 20, a bone 299 is shown with a fracture 299F and focal bone lesion 299L. An internal medical scaffold 205I is in vivo deployed in the medullary cavity of the bone 299 and an external medical scaffold 205E is deployed by surrounding the exterior of the bone 299 and the fracture 299F. In some embodiments, the medical scaffold 205 is employed to fuse, join or weld the fractures 299F to one another. Another medical scaffold 205L is in vivo deployed in and around the focal bone lesion 299L. The bone 299 is shown with bone wear surface 299W thereon. A surface mounted medical scaffold 205W is deployed in vivo on the wear surface 299W of the bone 299 to confirm with mapping and imaging of the bone wear surface 299W, mating surfaces and areas proximate thereto. The biologically engineered substance, as described herein, is employed to promote vascularization, bone grown and tissue growth in cooperation with the internal medical scaffold 205I, the external medical scaffold 205E and the surface mounted medical scaffold 205W.

Figure 21:
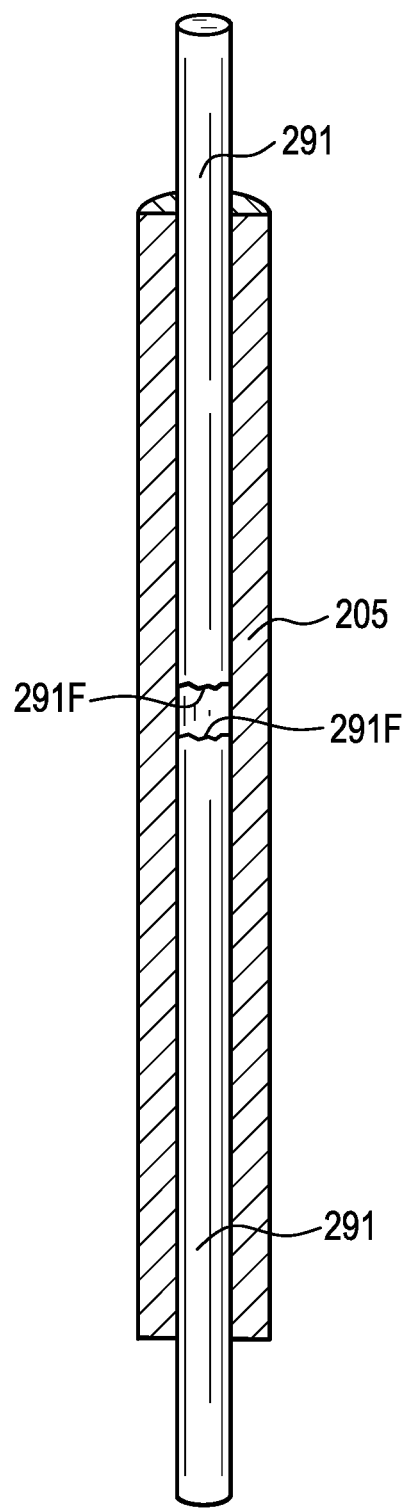
FIG. 21 is a schematic view of a torn nerve with a tubular medical scaffold therearound.

As shown in FIG. 21, a nerve 291 is shown with fractured ends 291F that define a damaged nerve site. A tubular medical scaffold 205 is deployed around the damaged nerve site so that portions of the nerve 291 and the fractured ends 291F are contained within an interior area of the tubular medical scaffold 205. The imaging system 242A and the sensor system 242B are employed to in vivo image, measure and map the damaged nerve site and to determine parameters for the tubular medical scaffold 205. The tubular medical scaffold is in vivo formed around the damaged nerve site. The biologically engineered substance, disclosed herein, is employed, for example, by applying the biologically engineered substance to an interior surface of the tubular medical scaffold 205 to cause the nerve to grow into the tubular medical scaffold 205 and rejoining of the fractured nerve ends 291F.

A method for performing in vivo procedures includes: accessing the target site, for example, endoscopically, visualize the density of materials in target site; viewing images on a computer display; and assessing where medical scaffold can be optimally placed. Additionally, the method includes, for example, 3D printing an object, e.g., medical scaffold, at a tissue defect, for example, in the case of a spinal procedure, between two vertebrae (in some embodiments, without need for additional materials such as plates, screws and rods), where the scaffold is customized to the patient. The procedure can use material such as the biologically engineered substance, as disclosed herein, deploy (e.g., flow, inject, paste) the biologically engineered substance in and/or around medical scaffold. Optionally, the method can further include creating voids in adjacent tissue, for example, in the case of a spine, in the adjacent vertebra, and applying a substance to the voids to provide additional stability. In some embodiments, the scaffold can be created ex vivo and subsequently implanted. In some embodiments, the method can be performed in a single procedure.

There is disclosed herein a method for performing in vivo procedures. The method includes providing a control unit 210 having a computer processor 212 and a robotic arm 240 in communication with the control unit 212. The robotic arm 240 has a casing that has a plurality of passages 240P therein. A printer head 242E is disposed in the opening 242E of one of the plurality of passages 240P. A imaging system 242A is disposed in the opening 214A one of the plurality of passages 240P. A sensor system 242B is disposed in the opening 241B of one of the plurality of passages 240P. The computer processor 212 is in communication with the printer head 242E, the imaging system 242A and the sensor system 242B. The computer processor 212 has executable software 214 therein which is configured for receiving signals from the imaging system 242A and the sensor system 242B.

The method includes in vivo measuring, via the imaging system 242A, a cavity 250C for receiving an object 205 and to obtain measurements of the cavity 250C. The method includes in vivo mapping, via the imaging system 242A, a receiving surface 260F for receiving the object 205 to obtain a surface map. The method also includes in vivo ascertaining, via the sensor system 242B, properties of the receiving surface 260F and areas proximate thereto. The method includes ascertaining, via the sensor system 242B, at density, hardness and/or chemical composition of the receiving surface 260F and areas proximate thereto. The executable software 214 correlates the cavity measurements, the surface map and the properties of the receiving surface 260F and areas proximate thereto, to generate installation parameters. The method further includes creating, via the printer head 242E, the object 205 in vivo based upon the installation parameters. The object 205 is positioned in a predetermined patient specific in vivo location, based upon the installation parameters.

In some embodiments, the method includes providing a coating deployment system 242C disposed in the opening 241C of one of the plurality of passages 240P. The method includes having the coating deployment system in vivo apply a biologically engineered substance to object 205 and/or the receiving surface 260F. The biologically engineered substance can include one or more of the following: (a) a vascularization promoting substance; (b) a growth factor substance; (c) an immune reaction deterrent substance; (d) a bone regeneration substance; and/or a tissue regeneration substance. The method can include disposing the biologically engineered substance in the coating deployment system 242C; and applying the biologically engineered substance to the object 205 and the receiving surface 260F.

The method includes providing a curing device 242D in the opening 241D of one of the plurality of passages 240P; and in vivo curing and/or un-curing the object 205, via the curing device 242D, for example using ultraviolet systems and/or laser systems.

In some embodiments, the method includes providing a post-positioning monitoring system 277A and a post-positioning alteration system 277B, each being in communication with the computer processor 212. The method includes monitoring, via the post-positioning monitoring system, 277A positions of the object 205 relative to the receiving surface 260F after in vivo placement of the object 205. The method further includes transmitting the positions of the object 205 to the computer processor 212; evaluating the positions of the object 205, via the executable software 214; and determining, via the executable software 214, the adequacy of the positions of the object 205. The executable software 214 generates commands to the post-positioning alteration system 277B; and the positions of the object 205 is altered based upon the commands.

As an example, the method can be employed for forming object 205 positioned between adjacent vertebral bodies 220A in the cavity 250C, located between the adjacent vertebral bodies 220A. In one embodiment, the receiving surface 260F is on the adjacent vertebral bodies 220A. In one embodiment, the method is employed for in vivo repairing of damaged hard bone or cartilage. In one embodiment, the method is employed for in vivo reconstruction of hard bone comprising in vivo reshaping the hard bone by in vivo forming and erecting the medical scaffold on a surface of the hard bone. In one embodiment, the method is employed for in vivo repair of a damaged ligament site, comprising imaging the damaged site and determining parameters for a medical scaffold and in vivo forming and erecting the medical scaffold in the damaged site such that the medical scaffold expands and contracts with the ligament and to urge a first torn ligament end towards a second torn ligament end. In one embodiment, the method is employed for in vivo repair of soft tissue. In one embodiment, the method is employed for in vivo nerve repair.

While the systems and methods herein have been described primarily for spinal applications, these can be applied to various hard and soft tissue applications. Objects in hard tissue applications can include a hard, bone-like object with an added material to recruit bone growth, such as a biologically engineered substance, the ability to selectively vascularize some or all of the scaffold (for example, in meniscus applications) and the ability to adjust the scaffold, for example via curing/uncuring at time subsequent to deployment. Exemplary applications include: (1) cartilage repair such as repairing a torn meniscus including deploying a medical scaffold 205 that has cartilage-like properties and selectively creating a vascularized portion 205V of the medical scaffold 205 that has a plurality of vascular passages 205Q selectively formed therein as discussed herein with reference to FIGS. 19A and 19B; (2) bone 299 fracture 299F and/or focal bone lesion 299L repair including the in vivo deployment of an internal medical scaffold 205I in the medullary cavity of the bone 299 and/or an external medical scaffold 205E surrounding the exterior of the bone 299 and the fracture 299F and in vivo deploy another medical scaffold 205L in and around the focal bone lesion 299L, as shown in FIG. 20 and employing a biologically engineered substance to promote vascularization, bone grown and tissue growth, as described herein; (3) bone wear surface 299W reshaping (e.g., hip or knee bone reshaping, facial bone reconstruction, nose bone reshaping, cheek and chin bone reshaping and jaw reshaping) including the in vivo deployment of a surface mounted medical scaffold 205W on the surface of the bone 299 to confirm with mapping and imaging of the bone wear surface 299W, mating surfaces and areas proximate thereto, as shown in FIG. 20 and employing a biologically engineered substance to promote vascularization, bone grown and tissue growth, as described herein; (4) forming of post sites in bone such as via drilling holes in bone for placement of posts to be secured with a bone compatible adhesive; (5) fusing vertebra to one another; and (6) eliminating micro-motion after deployment of the scaffold.

Objects in soft tissue applications can be soft, for example a structurally stable yet deformable scaffold that moves with the adjacent anatomy, the ability to selectively vascularize some or all of the scaffold, for example via a coating, the ability to adjust the scaffold, for example via curing/uncuring at times subsequent to deployment. Examples of these types of scaffolds are shown in FIGS. 14A-14G. Exemplary applications include: (1) ligament repair 297 of a torn ligament (e.g., torn anterior cruciate ligament (ACL) or torn medial patellofemoral ligament (MPFL)) wherein a medical scaffold 205 with a tensioner 205T is secured between two ends 297A' and 297B' of the torn ligament 297 to urge the two ends 297A' and 297B' to one another to promote healing and curing of the torn ligament, as described herein with respect to FIG. 19C and a biologically engineered substance is employed to promote vascularization and tissue growth to promote rejoining of the two ends 297A' and 297B' to one another, as described herein; (2) dermal repair including treatment of burns and deceased skin and use of collagen based scaffolds to retain skin elasticity and provide structural support relative to tissue and muscle; (3) adipose repair (e.g., breast reconstruction, fat loss reconstruction, and cancer caused tissue loss) to mitigate tissue and bone volume loss by mapping and imaging a target area and in vivo forming the medical scaffold 205 in a predetermined location based upon the mapping and imaging; (4) peripheral nerve surgery including providing an in vivo imaging system and an in vivo printer head; imaging a damaged site of a nerve using the in vivo imaging system to determine parameters for a tubular medical scaffold; in vivo forming and erecting the tubular medical scaffold around the damaged site; and employing a biologically engineered substance, for example applying the biologically engineered substance to an interior surface of the tubular medical scaffold to cause the nerve to grow into the tubular medical scaffold, as described herein with reference to FIG. 21; (5) abdominal or scrotal hernia repair using the multifunctional robotic system 200 to form, either ex vivo or in vivo, a mesh and deploying the mesh in the body; (6) bronchial repair procedures wherein the medical scaffold is customized in fit and size based upon in vivo imaging and sensing consistent with patient specific bronchial anatomy and wherein the medical scaffold is flexible and is configured to expand in response to a patient's coughing; and (7) real time tracking of surgical procedures, including the use of electromagnetic systems to track in vivo movement of the medical scaffold and body parts connected thereto.

While the system and methods herein have been described to printing the object in vivo, the object can also be printed ex vivo and subsequently implanted.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Furthermore, the embodiments disclosed herein may be combined with one another in any combination or stand alone. Therefore, it is intended that the invention not be limited to the particular embodiments disclosed in the above detailed description, but that the invention will include all embodiments falling within the scope of the appended claims.

Although the present invention has been disclosed and described with reference to certain embodiments thereof, it should be noted that other variations and modifications may be made, and it is intended that the following claims cover the variations and modifications within the true scope of the invention.

What is claimed is:

1. A multifunctional robotic system for performing in vivo procedures, the robotic system comprising:
   a control unit comprising a computer processor;
   a robotic arm in communication with the control unit for multi-axis movement of the robotic arm, the robotic arm comprising a casing having a plurality of passages therein;
   a printer head disposed in and configured to operate from at least one of the plurality of passages, the printer head being configured to create at least one multi-dimensional object;
   a measuring system disposed in and configured to operate from at least one of the plurality of passages;
   wherein the computer processor is in communication with the printer head and the measuring system, and the computer processor comprises executable software configured to receive signals from the measuring system, the executable software being configured to control the printer head and the measuring system to position the object in an in vivo location based upon the signals from the measuring system.

2. The robotic system of claim 1, wherein the measuring system comprises an imaging system configured to in vivo measure a cavity for receiving the object and mapping a receiving surface in the cavity.

3. The robotic system of claim 1, wherein the measuring system comprises a sensor system disposed in and configured to operate from at least one of the plurality of passages, the sensor system being configured to ascertain properties of a receiving surface and areas proximate thereto.

4. The robotic system of claim 1, wherein the positioning of the object comprises forming the object in vivo.

5. The robotic system of claim 1, wherein the positioning of the object comprises forming the object ex vivo.

6. The robotic system of claim 1, further comprising at least one ex-vivo formed segment of the object and wherein at least one of the passages comprises a conveyor system for transporting the segment to the cavity.

7. The robotic system of claim 1, wherein the casing is configured to fit in a lumen of a body.

8. The robotic system of claim 2, wherein the imaging system comprises at least one of a magnetic resonance imaging system, a spectral imaging system, and a computed topography system.

9. The robotic system of claim 1, further comprising a coating deployment system disposed in and configured to operate from at least one of the plurality of passages, the coating deployment system being configured to in vivo apply a biologically engineered substance to at least one of the object and a receiving surface.

10. The robotic system of claim 1, further comprising a biologically engineered substance.

11. The robotic system of claim 10, wherein the biologically engineered substance is at least one of:
 (a) applied to the object in vivo;
 (b) applied to the object ex vivo;
 (c) flowable;
 (d) injectable;
 (e) a putty;
 (f) a paste;
 (g) a powder;
 (h) applied to area proximate to the object;
 (i) forms at least a portion of the object;
 (j) printable via the printer head; and
 (k) in vivo and ex vivo curable.

12. The robotic system of claim 10, wherein the biologically engineered substance comprises at least one of:
 (a) a vascularization promoting substance;
 (b) a growth factor substance;
 (c) an immune reaction deterrent substance;
 (d) a bone regeneration substance; and
 (e) a tissue regeneration substance; and
wherein the biologically engineered substance is disposed in and applied from a coating deployment system.

13. The robotic system of claim 1, wherein the printer head comprises a material discharge port for in vivo discharging material for in vivo building of the object.

14. The robotic system of claim 13, wherein the object comprises a plurality of layers of the material formed additively upon one another to establish a predetermined size of the object based upon a properties of a receiving surface and a areas proximate thereto.

15. The robotic system of claim 1, further comprising a material removal system disposed in at least one of the plurality of passages and wherein the material removal system is configured to establish a predetermined size of the object based upon a properties of a receiving surface and a areas proximate thereto.

16. The robotic system of claim 1, wherein at least one of the passages comprises an assembly system and wherein the object comprises a plurality of segments each having an interlocking system thereon and wherein the assembly system is configured to in vivo assemble the segments to one another and to lock the interlocking systems of adjacent segments to one another.

17. The robotic system of claim 1, further comprising an optical device disposed in and configured to operate from at least one of the plurality of passages, the optical device being in communication with the computer processor to transmit in vivo images to the computer processor.

18. The robotic system of claim 1, further comprising a curing device disposed in and configured to operate from at least one of the plurality of passages, the curing device being configured to in vivo cure material deposited in a body cavity.

19. The robotic system of claim 18, wherein the curing device comprises at least one of a laser, a heat source and a chemical reactant.

20. The robotic device of claim 1, further comprising a multi-axis positioner disposed in and configured to operate from at least one of the plurality of passages, the multi-axis positioner being in communication with the printer head and the computer processor to control dynamic positioning of the printer head in vivo.

21. The robotic system of claim 1, wherein at least one of the passages compromises a heat sink, a material evacuation system, a coolant deployment system and an insulation system.

22. The robotic system of claim 1, wherein the robotic arm compromises a sterile interface for mitigating infection caused by in vivo deployment of the object.

23. The robotic system of claim 3, wherein the sensor system is configured to ascertain at least one of density, hardness, and chemical composition.

24. The robotic system of claim 1, further comprising at least one in vivo miniaturized medical device in communication with the computer processor.

25. The robotic system of claim 24, further comprising an interactive group of in vivo miniaturized medical devices in communication with the computer processor.

26. The robotic system of claim 1, further comprising at least one of a post-positioning monitoring system and a post-positioning alteration system, each being in communication with the computer processor, the post-positioning monitoring system being configured to monitor the position of the object relative to a receiving surface and the post-positioning alteration system being configured to reposition and alter the object.

27. The robotic system of claim 26, wherein at least one of the imaging system, the sensor system, the post-positioning monitoring system and the post-positioning alteration system is located in the object.

28. The robotic system of claim 26, wherein at least one of the printer head, the imaging system, the sensor system, the post-positioning monitoring system and the post-positioning alteration system is located in at least one miniaturized medical device in an in vivo configuration.

29. The robotic system of claim 1, wherein the system is configured to be deployed via an endoscope.

* * * * *